(12) United States Patent
Price

(10) Patent No.: US 12,008,752 B2
(45) Date of Patent: Jun. 11, 2024

(54) AUTOMATED SCAN OF COMMON AILMENTS SO THAT A CONSISTENT IMAGE CAN BE GIVEN TO A DOCTOR FOR ANALYSIS

(71) Applicant: Amazon Technologies, Inc., Seattle, WA (US)

(72) Inventor: Layne Christopher Price, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 361 days.

(21) Appl. No.: 17/362,018

(22) Filed: Jun. 29, 2021

(65) Prior Publication Data

US 2022/0414866 A1    Dec. 29, 2022

(51) Int. Cl.
| | | |
|---|---|---|
| *G06N 3/08* | (2023.01) | |
| *G06T 7/00* | (2017.01) | |
| *G06T 7/73* | (2017.01) | |
| *G16H 30/40* | (2018.01) | |
| *G16H 40/67* | (2018.01) | |
| *H04W 4/02* | (2018.01) | |

(52) U.S. Cl.
CPC ............. *G06T 7/0012* (2013.01); *G06N 3/08* (2013.01); *G06T 7/74* (2017.01); *G16H 30/40* (2018.01); *G16H 40/67* (2018.01); *H04W 4/026* (2013.01); *G06T 2207/10016* (2013.01); *G06T 2207/20081* (2013.01); *G06T 2207/20084* (2013.01)

(58) Field of Classification Search
CPC .................... G06T 7/0012; G06T 7/74; G06T 2207/10016; G06T 2207/20081; G06T 2207/20084; G06N 3/08; G06N 3/045; G16H 30/40; G16H 40/67; G16H 40/63; G16H 80/00; H04W 4/026
USPC ........................................................ 382/128
See application file for complete search history.

(56) References Cited

U.S. PATENT DOCUMENTS

| | | | |
|---|---|---|---|
| 2014/0300722 | A1 | 10/2014 | Garcia |
| 2014/0313303 | A1 | 10/2014 | Davis et al. |
| 2020/0327670 | A1 | 10/2020 | Connor |
| 2022/0051409 | A1* | 2/2022 | Maclellan .............. G16H 50/70 |

OTHER PUBLICATIONS

International Search Report and Written Opinion, PCT App. No. PCT/US2022/034763, dated Oct. 13, 2022, 12 pages.
International Preliminary Report on Patentability, PCT App. No. PCT/US2022/034763, Jan. 11, 2024, 10 pages.

* cited by examiner

*Primary Examiner* — Charlotte M Baker
(74) *Attorney, Agent, or Firm* — Nicholson De Vos Webster & Elliott LLP

(57) ABSTRACT

Techniques for automated alignment of image capture of physical ailments are described. A method of automated alignment of image capture of physical ailments includes determining an alignment class of a first image of an object using an alignment classifier executing on a user device, providing alignment instructions based on the alignment class and a reference image associated with the object using at least one machine learning model executing on the user device, obtaining an aligned image of the object after the user device has been repositioned relative to the object based on the alignment instructions, and sending the aligned image to an agent device via a telemedicine service of a provider network.

20 Claims, 14 Drawing Sheets

AUTOMATED SCAN OF COMMON AILMENTS SO THAT A CONSISTENT IMAGE CAN BE GIVEN TO A DOCTOR FOR ANALYSIS

BACKGROUND

Telemedicine systems enable doctors, nurses, and other healthcare providers to interact with patients who are not physically present, via phone, videoconference, or other means. This has become a more accessible option as increasing numbers of people carry video chat enabled smartphones, web cam-equipped personal computers, etc. Any distractions between the provider and the patient during the call can lead to a poor call experience as well as misdiagnoses and misunderstandings. As such, video and audio quality are important in such interactions to ensure clear communications between the health care provider and the patient. Additionally, the doctor is limited to the information that the patient can describe or show using their electronic device. As such, the patient needs to be able to effectively capture images of whatever ailment they are experiencing in sufficient detail for the doctor to make a proper diagnosis.

If the doctor is aware that the image or video that they are receiving inadequately captures the ailment, then they may instruct the patient to capture the image again. However, such manual instruction can be difficult for the doctor to communicate and for the patient to accurately perform. may be difficult for the patient to effectively communicate. Existing telemedicine systems provide limited feedback to the patient capturing the images. This leads to frustrating telemedicine experiences for both the patient and the doctor and can potentially lead to misdiagnoses and other mistakes.

BRIEF DESCRIPTION OF DRAWINGS

Various embodiments in accordance with the present disclosure will be described with reference to the drawings, in which.

DETAILED DESCRIPTION

The present disclosure relates to methods, apparatus, systems, and non-transitory computer-readable storage media for using machine learning to assist in the capture of image data of medical ailments to improve telemedicine communication. According to some embodiments, a machine learning model running on a user device monitors a video feed while the device's camera is being used to take a picture of a medical ailment. For example, the patient may be attempting to capture the image of a cut, rash, mole, etc. The machine learning model compares the video to an annotated reference library of photos of medical conditions. After finding an appropriate reference, instructions are given to the patient to reorient their device relative to the ailment to best match the reference image. The best-fitting real-life photo and the chosen reference images are sent to a telemedicine doctor who is linked to the patient via a video feed. The two images are presented side-by-side to the doctor for their review and to aid in clinical diagnosis.

Figure 1:
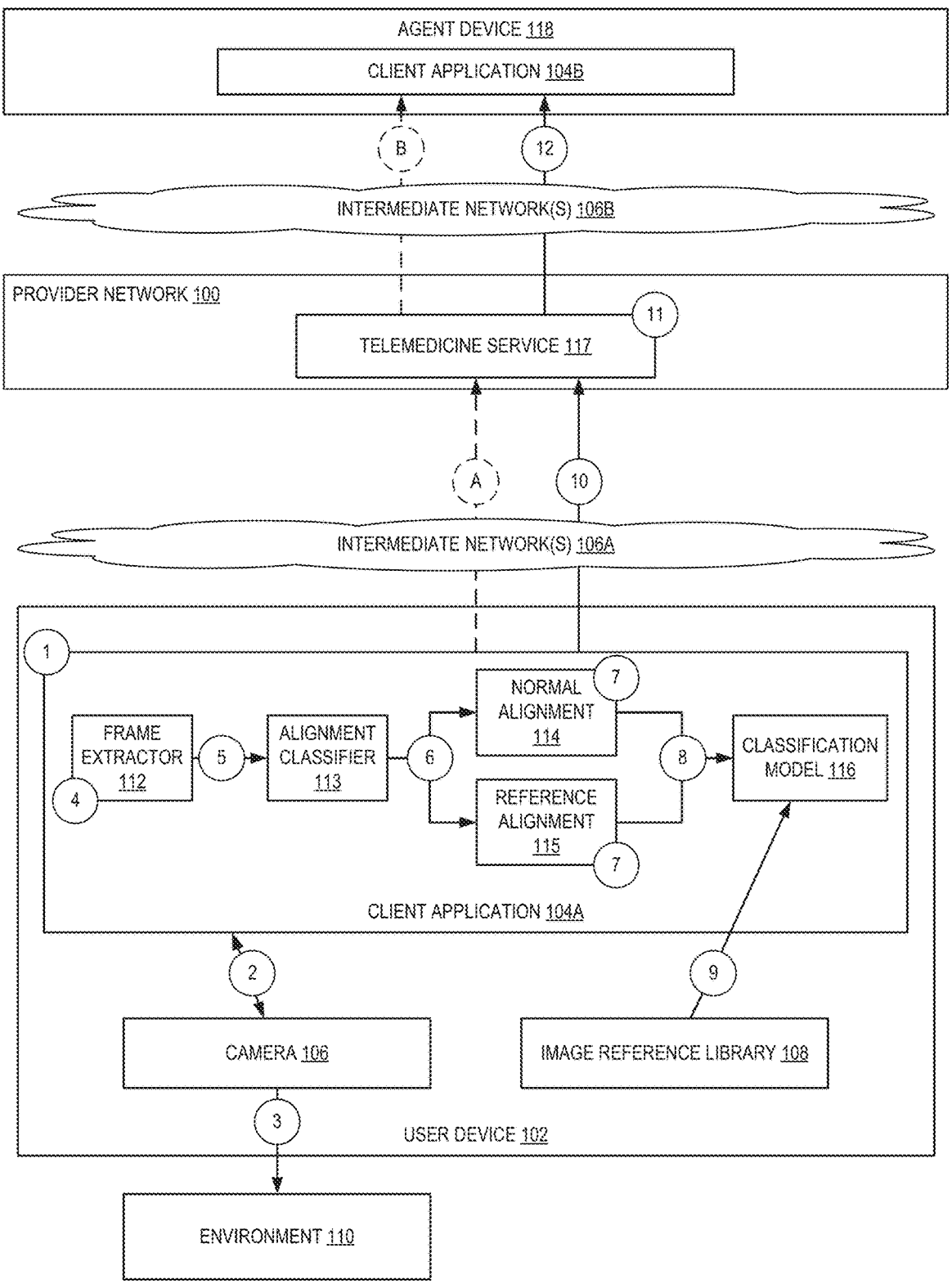
FIG. 1 is a diagram illustrating an environment for automated alignment of image capture of physical ailments according to some embodiments.

FIG. 1 is a diagram illustrating an environment for automated alignment of image capture of physical ailments according to some embodiments. As shown in FIG. 1, a user device 102, such as a phone, tablet, laptop computer, desktop computer, or other computing device, can include a client application 104A. The client application 104A may include a web browser, teleconferencing application, telemedicine client application, or other application executing thereon, through which a user may contact an agent, such as a doctor, nurse, or other telemedicine provider. Although embodiments are described with respect to telemedicine providers, embodiments may be implemented in various teleconferencing domains. As shown in FIG. 1, the user device 102 may also include a camera 106 and a reference image library 108. The camera can include any image capture device capable of capturing image stills and/or video. In some embodiments, the user device 102 may include multiple cameras. For example, a phone or tablet may include one or more front-facing and one or more rear-facing cameras. The reference image library 108 may include images of ailments (e.g., rashes, cuts, contusions, discolorations, or other visible physical maladies), under various lighting conditions and being experienced by various different people, that have been labeled by experts (e.g., doctors or other specialists) and which represent exemplars of those ailments.

Using the client application 104A, the user may initiate a telemedicine session. In some embodiments, this is performed by opening the client application 104A, at numeral 1. For example, the user may select an icon or other user interface element associated with the client application 104A to open the application on user device 102. Once opened, the client application 104A can begin capturing image data using camera 106 at numeral 2. In some embodiments, the client application 104A may include a user interface element which, when selected by the user, causes the camera 106 to begin streaming video of the environment 110. For example, the client application 104A may include an icon that indicates "ailment capture" or similar. Once the camera 106 begins capturing image data of environment 110, at numeral 3, the image data can be used by the client application 104A to identify the user's ailment and instruct the user to align the user device 102 with the ailment to improve the representation of the ailment captured in the image data. The environment 110 may include the general location where the user device is located as well as parts of the user's body which the user is recording to provide an example of the ailment to the telemedicine provider for review.

In various embodiments, as described above, the patient may begin capturing images of their ailment as soon as they open the client application. Alternatively, the patient may first establish a session with a telemedicine provider before capturing any image data. In such embodiments, when the user opens the application 104A, the user may provide a log in credential (e.g., username and password, biometric information, or other security credential) to verify their identity. Once verified, the client application 104A can attempt to establish a connection with a provider. For example, at circle A, the client application can send a request to telemedicine service 117 to be connected to a provider. In various embodiments, the request may be made using one or more application programming interfaces (APIs), such as a representational state transfer (REST) API, or other web services API. The telemedicine service can then route the patient's request to a specific agent device 118 used by a telemedicine provider, at circle B. As shown, the agent device 118 may include a client application 104B, which may include a web browser, teleconferencing application, telemedicine, or other application executing thereon, through which an agent can respond to calls from a patient. In some embodiments, the agent's client application 104B and the patient's client application 104A may be the same application or may provide specific agent or patient functionality, respectively. Once the telemedicine call has been established, the patient may then begin collecting image data using the client application 104A and camera 106, as discussed.

In some embodiments, encryption may be performed using various encryption techniques when establishing, maintaining, and ending a session between a patient and an agent. In some embodiments, the encryption technique used may be selected to meet standards for handling personal health information (PHI) securely, such as Advanced Encryption Standard (AES) 128, 192 or 256-bit encryption, OpenPGP, S/MIME, etc. Such encryption may further enable compliance with regulations governing the secure handling of personal health information (PHI), such as the Health Insurance Portability and Accountability Act (HIPAA) or other regulations.

A provider network 100 (or, "cloud" provider network) provides users with the ability to use one or more of a variety of types of computing-related resources such as compute resources (e.g., executing virtual machine (VM) instances and/or containers, executing batch jobs, executing code without provisioning servers), data/storage resources (e.g., object storage, block-level storage, data archival storage, databases and database tables, etc.), network-related resources (e.g., configuring virtual networks including groups of compute resources, content delivery networks (CDNs), Domain Name Service (DNS)), application resources (e.g., databases, application build/deployment services), access policies or roles, identity policies or roles, machine images, routers and other data processing resources, etc. These and other computing resources can be provided as services, such as a hardware virtualization service that can execute compute instances, a storage service that can store data objects, etc. The users (or "customers") of provider networks 100 can use one or more user accounts that are associated with a customer account, though these terms can be used somewhat interchangeably depending upon the context of use. Users can interact with a provider network 100 across one or more intermediate networks 106A and 106B (e.g., the internal via one or more interface(s), such as through use of application programming interface (API) calls, via a console implemented as a website or application, etc. An API refers to an interface and/or communication protocol between a client and a server, such that if the client makes a request in a predefined format, the client should receive a response in a specific format or initiate a defined action. In the cloud provider network context, APIs provide a gateway for customers to access cloud infrastructure by allowing customers to obtain data from or cause actions within the cloud provider network, enabling the development of applications that interact with resources and services hosted in the cloud provider network. APIs can also enable different services of the cloud provider network to exchange data with one another. The interface(s) can be part of, or serve as a front-end to, a control plane of the provider network 100 that includes "backend" services supporting and enabling the services that can be more directly offered to customers.

For example, a cloud provider network (or just "cloud") typically refers to a large pool of accessible virtualized computing resources (such as compute, storage, and networking resources, applications, and services). A cloud can provide convenient, on-demand network access to a shared pool of configurable computing resources that can be programmatically provisioned and released in response to customer commands. These resources can be dynamically provisioned and reconfigured to adjust to variable load. Cloud computing can thus be considered as both the applications delivered as services over a publicly accessible network (e.g., the Internet, a cellular communication network) and the hardware and software in cloud provider data centers that provide those services.

To provide these and other computing resource services, provider networks 100 often rely upon virtualization techniques. For example, virtualization technologies can provide users the ability to control or use compute resources (e.g., a "compute instance," such as a VM using a guest operating system (O/S) that operates using a hypervisor that might or might not further operate on top of an underlying host O/S, a container that might or might not operate in a VM, a compute instance that can execute on "bare metal" hardware without an underlying hypervisor), where one or multiple compute resources can be implemented using a single electronic device. Thus, a user can directly use a compute resource (e.g., provided by a hardware virtualization service) hosted by the provider network to perform a variety of computing tasks. Additionally, or alternatively, a user can indirectly use a compute resource by submitting code to be executed by the provider network (e.g., via an on-demand code execution service), which in turn uses one or more compute resources to execute the code—typically without the user having any control of or knowledge of the underlying compute instance(s) involved.

In various embodiments, an on-demand code execution service (referred to in various embodiments as a function compute service, functions service, cloud functions service, functions as a service, or serverless computing service) can enable customers of the provider network 100 to execute their code on cloud resources without having to select or manage the underlying hardware resources used to execute the code. For example, a customer can use the on-demand code execution service by uploading their code and use one or more APIs to request that the service identify, provision, and manage any resources required to run the code.

Once image data is being collected by camera 106, it is received by client application 104A. For example, the image data may be received as digital video data which comprises a plurality of digital image frames. To capture the image data, the patient may position their device 102 (e.g., smartphone, tablet, or other device capable of capturing image data) over their ailment such that the ailment is within the device's field of view. A frame extractor 112 can extract individual frames from the digital video at numeral 4. In some embodiments, the frame extractor 112 can analyze individual frames to determine whether there are any obvious defects which would prevent the frame from being further analyzed. For example, is the frame out of focus, overexposed, underexposed, etc. The frames are then provided to an alignment classifier 113, at numeral 5.

As discussed, embodiments look up a library of images of common ailments and identifies how to re-orient the ailment in the camera field of view (via translation and rotation of the user device relative to the subject) until it most closely matches the orientation of the reference images. This may be based on the size of the ailment relative to the reference and the angle of the camera relative to the ailment. Additionally, the type of alignment that can be performed may vary depending on the ailment. For example, reference images may be divided into two classes: (1) those where the surface of the camera is aligned to the surface of the photo subject so that they are parallel; and (2) those where reference points in the real time photo are aligned with reference points in a reference image. Alignment classifier 113 determines, for a given input frame from frame extractor 112, whether the image corresponds to a normal alignment class or a reference point alignment class. The alignment classifier 113 may be a machine learning model, such as a convolutional neural network (CNN)-based model, which has been trained to classify a given input image into either of these classes. The training data may include the image reference library 108, or similar dataset, which has been labeled with one of these two classes. Alternatively, the alignment classifier may determine a reference image most likely to match the input image. In such instances, each reference image may be associated with an alignment type (e.g., normal alignment or reference point alignment) and the alignment type to be performed is based on the alignment type associated with the reference image.

At numeral 6, depending on the class of the input frame, the frame is provided to normal alignment manager 114 or reference alignment manager 115. At numeral 7, the appropriate alignment manager helps the patient align their device with the ailment so as to improve the image quality of the captured image. An aligned image is then captured and cropped to the ailment. The resulting image is then provided to classification model 116 at numeral 8. Classification model 116 then matches the aligned image with images from image reference library 108, at numeral 9. For example, the classification model 116 may determine a probability of a match between the input image and the reference images and rank the reference images based on the predicted probability of a match. In some embodiments, photometric calibration is performed on the patient images based on the reference images. For example, the color, contrast, etc. of the patient image is adjusted based on the settings of the images in the image reference library 108. Additionally, the reference image library includes images of ailments captured under a variety of lighting conditions and a variety of skin tones. In some embodiments, the image reference library includes images of ailments that have been isolated from the surrounding tissue. In some embodiments, the reference images may be transformed to remove personal identifiable information (PII). For example, faces may be blurred, or other image transformations may be applied to the reference images before they are added to the reference library in full compliance with HIPAA or other regulations.

Doing color correction correctly is important, as the specific colors of some ailments (e.g., rashes, etc.) are relevant to an accurate assessment of the ailment. In some embodiments, color correction could be done by first segmenting the image with a trained CNN, obscuring any interesting segments that are not shared between the field image and the reference image (e.g., the wound or the background), and adjusting global RGB values in the field image to match the non-obscured regions of the reference image most closely.

At numeral 10, if a session has not already been established with a provider, then the client application 104A sends a request to telemedicine service 117 to connect to a provider. At numeral 11, the telemedicine service connects the patient to a provider, as discussed further below. At numeral 12, the aligned and color corrected image is sent to the provider, who views the image on their agent device 118 and provides an analysis of the image to the patient. For example, the provider may use the image to diagnose the patient and prescribe a course of action. Alternatively, if a session has already been established (e.g., at circles A and B, described above), then the image is provided to the provider directly via the already established videoconference link, without further connection management via the telemedicine service 117 required.

As discussed further, in a telemedicine setting, the doctor/practitioner will be on a videoconference with the patient and will have the patient's video on the monitor. In some embodiments, the image of the ailment may be overlaid on the screen of the agent device 118 such that the provider can examine the ailment at length while communicating eye-to-eye with the patient, picture-in-picture style. Additionally, in some embodiments, the provider can scroll through multiple reference images and compare to the ailment image side-by-side. In some embodiments, the reference images may be ranked according to the likelihood of a match determined by classification model 116.

Figure 2:
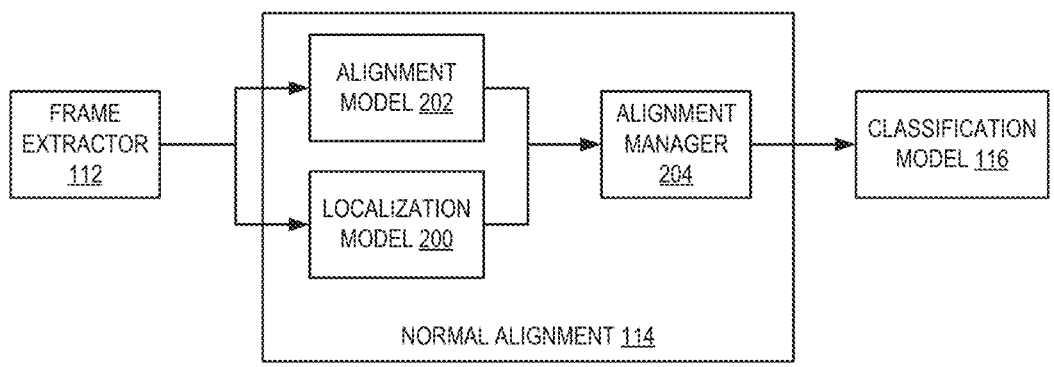
FIG. 2 is a diagram illustrating surface normal alignment according to some embodiments.

FIG. 2 is a diagram illustrating surface normal alignment according to some embodiments. As discussed, when an input image is determined to be of a class that can be aligned via the surface normal of the tissue and the surface normal of the user device, then alignment may be determined by normal alignment manager 114. As shown in FIG. 2, the frames are extracted from an input video captured by the camera and provided to a localization model 200 and an alignment model 202. By analyzing the image data, an alignment procedure can be performed in which alignment instructions are provided to the patient to capture one or more images of the ailment.

For example, localization model 200 identifies a location of a likely ailment in the image data. The localization model may include a machine learning model, such as a convolutional neural network (CNN)-based model which has been trained to identify various ailments. For example, the image reference library 108 includes a plurality of images of ailments which have been labeled accordingly. During training, the localization model is trained using the image reference library 108, or a similar image library, to identify ailments in image data. In some embodiments, the localization model 200 annotates the image data with a bounding box or other localization information around the likely ailment.

The alignment model 202 can determine geometric parameters associated with the part of the body represented in the image data. Alignment model 202 may include a CNN-based machine learning model which has been trained to generate a geometric representation of a part of the body captured in the image data. Most parts of the body can be represented by rough cylindrical shapes. The alignment model is trained to generate cylindrical parameters of the portion of the body represented in image data. For example, the alignment model is trained using images and measurement data of peoples' bodies/body parts to analyze an image of a body part and output a model of that body part. When presented with an image including, e.g., a representation of a person's arm, the alignment model produces a cylindrical model of the arm in the picture. As a person's dimensions may vary by weight and height, in some embodiments the patient's height and weight may be encoded and included with the image data (concatenated with the image data and/or feature data extracted from the image data) to obtain a more accurate representation of the body part.

The geometric parameters of the body part represented in the image and the annotated image are provided to alignment manager 204. Alignment manager 204 can determine a surface normal vector associated with the ailment in the image data (e.g., at the location of the annotation in the image data). The alignment manager 204 generates instructions to change the orientation of the user device 102 based on the relative positions of the surface normal vectors. In some embodiments, the alignment manager 204 can implement various surface normal estimation techniques. For example, the alignment manager 204 may implement a deep surface normal estimation model. Such a model may include an RGB branch which analyzes the RGB channels of the image and a depth branch which analyzes a depth channel of the image. The result is a region of the image corresponding to the estimated normal vector. One example of such a model is described in Deep Surface Normal Estimation with Hierarchical RGB-D Fusion, Zeng, Jin and Tong, Yanfeng and Huang, Yunmu and Yan, Qiong and Sun, Wenxiu and Chen, Jing and Wang, Yongtian, Proceedings of the IEEE Conference on Computer Vision and Pattern Recognition, 2019. Additionally, or alternatively, the surface normal vector of the tissue may be identified based on the location of the ailment and the estimated geometric parameters of the body part depicted in the image. For example, techniques to estimate a surface normal of a point on a cylinder having cylinder parameters estimated for the depicted body part.

The estimated surface normal of the tissue is then aligned to the normal vector of the user device, which may be known experimentally and stored as part of client application 104A. For example, the normal vectors of various popular user devices may be determined offline and incorporated into the client application. At installation time, the user device is identified and the corresponding normal to that user device is stored for use during alignment. Alignment of the user device and the ailment may include changing the location of the user device in space (e.g., adjusting the x,y,z coordinates of the user device) or adjusting the attitude (e.g., yaw, pitch, and roll) of the user device relative to the ailment, to bring the surface normal vectors into alignment. For example, unitary transformation may be determined for aligning the user device and the ailment via one or more translations, rotations, etc. of the device with the ailment considered fixed. This processing may be performed iteratively on subsequent frames until the ailment and the user device are aligned. Once the alignment manager 204 determines that the user device is aligned, then the aligned image is provided to classification model 116 to be matched to a reference ailment from the image reference library.

Figure 3:
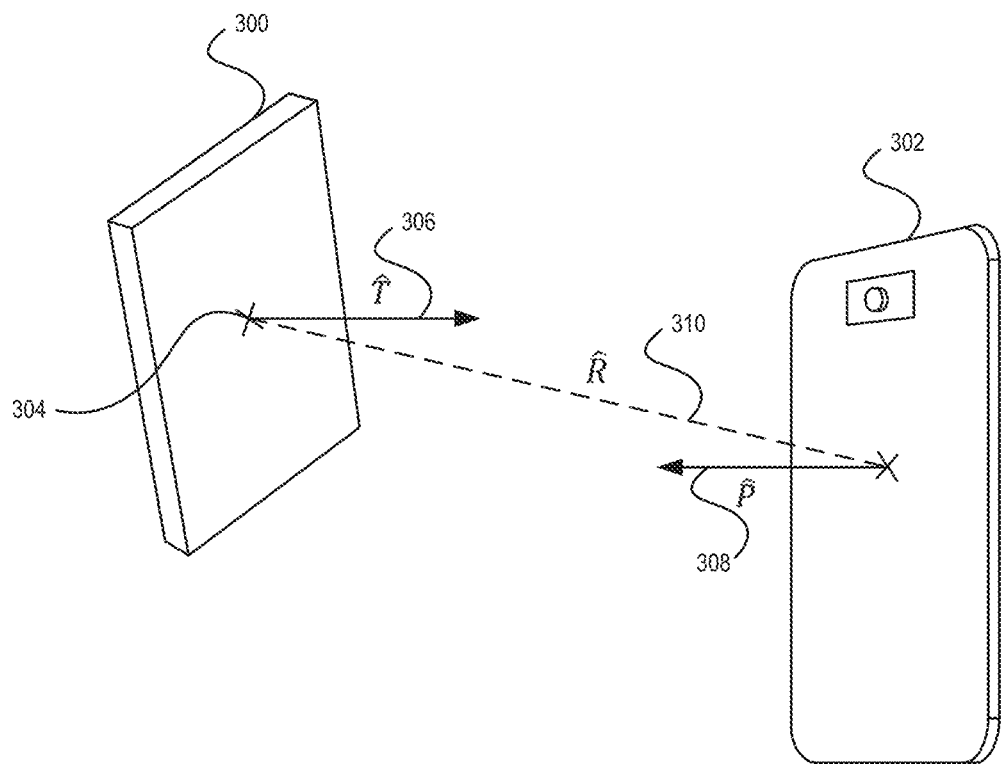
FIG. 3 is a diagram illustrating an alignment procedure according to some embodiments.

FIG. 3 is a diagram illustrating an alignment procedure according to some embodiments. As shown in FIG. 3, the patient may attempt to align a portion of their body, represented in this example by tissue 300, with their user device, represented in this example by smartphone 302. The tissue normal $\hat{T}$ 306 at the location of the is estimated by alignment manager 204, as discussed above, based on the input image. In some embodiments, the input image includes RGB and depth channels, and a machine learning model is used to analyze the RGB-D data and estimate $\hat{T}$. Alternatively, the estimated geometric parameters of the body part depicted in the image data may be used to estimate the tissue normal $\hat{T}$ 306 at the location of the ailment 304. The phone normal vector $\hat{P}$ 308 has been previously determined offline. A center of mass difference vector $\bar{R}$ is then calculated and converted to a unit vector $\hat{R}$ 310. For example, in some embodiments the center of mass difference vector $\bar{R}$ using the origins of the normal vectors for the tissue and the user device. Instructions are then generated automatically to be provided to the user (e.g., visually or audibly) to align $\hat{R}$ and $\hat{T}$ by moving the phone in space such that $\hat{R} \cdot \hat{T} \approx 1$. Then instructions are generated automatically to be provided to the user to adjust the attitude of the user device such that $\hat{P} \cdot \hat{T} \approx -1$. For example, a threshold value may be defined where if the dot product of $\hat{P}$ and $\hat{T}$ is within the threshold value of $-1$, and if the dot product of $\hat{R}$ and $\hat{T}$ is within the threshold value of 1, then the user device and ailment are considered aligned. Once aligned, the aligned image is used to classify the ailment, as discussed above.

Figure 4:
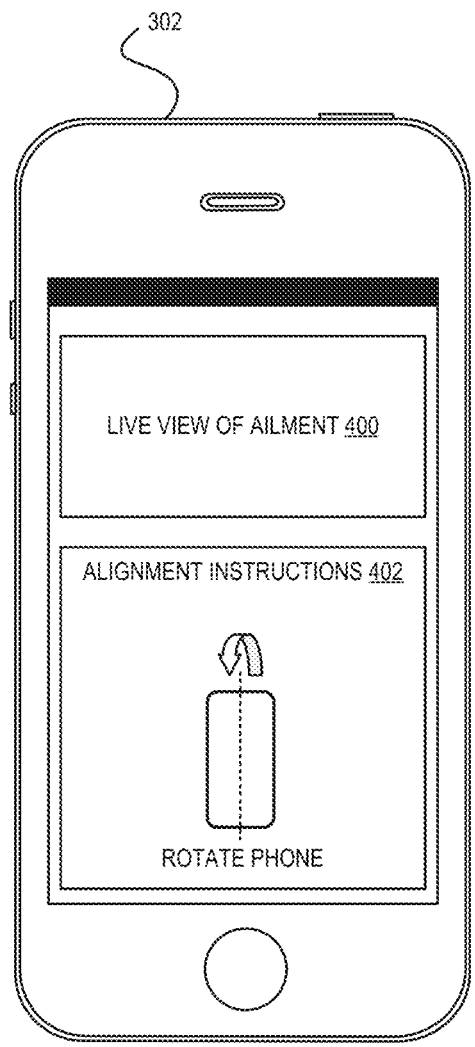
FIG. 4 is a diagram illustrating alignment feedback provided to a patient via an electronic device according to some embodiments.

FIG. 4 is a diagram illustrating alignment feedback provided to a patient via an electronic device according to some embodiments. As shown in FIG. 4, the user device 302 may display a live view of the image data 404. This may include a view of the ailment which the patient is attempting to capture an image of. Additionally, the user device may display alignment instructions 402. The alignment instructions may include instructions to move the user device in space (e.g., up, down, left, right, closer, farther, etc.) as well as instructions to change the attitude of the user device (e.g., rotate in a specific direction, adjust yaw/pitch/roll, etc.) relative to the ailment. In some embodiments, the instructions may be provided audibly rather than visually. For example, the user may be attempting to capture an ailment on their face, in their throat, or otherwise in a location that is difficult to capture while also viewing a screen of the user device. In such instances, visual instructions cannot be readily seen during alignment. Accordingly, the instructions may be produced audibly by the user device.

In some embodiments, the alignment instructions include visual cues to the patient to reconfigure the center of mass of the phone in the X, Y, Z directions, alter the pitch, yaw, and roll orientations of the phone, and/or adjust the camera's zoom settings. An example might be a blue arrow displayed on the user device in a particular direction that turns into a check mark whenever it is correctly aligned. Likewise, for attitude, a visualization of the movement of the user device may be shown. For example, in FIG. 4, the alignment instruction is to rotate the phone, and indicates the axis along which rotation is to be performed. In some embodiments, the instructions may be presented in order of priority. For example, position may be of higher priority than yaw/pitch/roll to ensure that the ailment is within the field of view of the camera. Once the device has been repositioned, then the next highest priority alignment may be performed.

Figure 5:
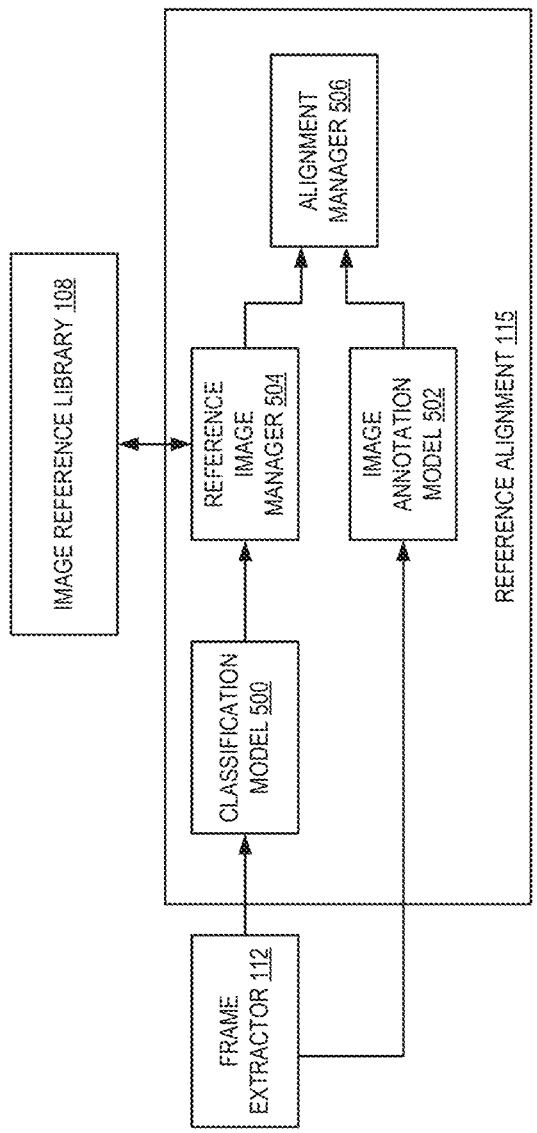
FIG. 5 is a diagram illustrating reference point alignment according to some embodiments.

FIG. 5 is a diagram illustrating reference point alignment according to some embodiments. As discussed, some ailments may be located where surface normal alignment is impractical or impossible. In such instances, reference alignment may be performed. When an input image is determined to be of a class that can be aligned via reference points, then alignment may be determined by reference alignment manager 115. As shown in FIG. 5, the frames are extracted from an input video captured by the camera and provided to classification model 500 and image annotation model 502.

Classification model 500 can be a CNN-based machine learning model trained to match an input image to a reference image. In some embodiments, classification model 500 may be the same model as classification model 116. Classification model 500 identifies a reference image from image reference library 108 that most closely matches the input image. Reference image manager 504 can then obtain the matching reference image from image reference library 108 and determine reference points associated with the reference image. In some embodiments, reference images that use reference point alignment may each be associated with three or more reference points. In some embodiments, the reference points may be stored as metadata associated with a corresponding reference image. In such instances, the reference image manager 504 reads the reference points from the metadata and provides the reference points to alignment manager 506. Alternatively, the reference image manager 504 can implement a trained CNN-based model can identify the reference points in the reference image. In either case, once the reference points have been identified from the reference image that most closely matches the input image, the reference points are provided to alignment manager 506.

As shown in FIG. 5, the input image is additionally provided to image annotation model 503. Image annotation model 502 may be a CNN-based model trained to identify reference points in images. In some embodiments, the image annotation model 502 may be the same model that was used to annotate the image reference library with reference points. Image annotation model 502 receives the input image and identifies a plurality of reference points in the image. The coordinates of the reference points in the image are provided to alignment manager 506.

Alignment manager 506 then compares the locations of the reference points in the reference image and the input image to determine how the user device should be moved to align the two images. Various matrix optimization techniques for point set alignment may be used to align the reference points of the reference image with the reference points of the input image, such as principal component analysis, singular value decomposition, or iterative closest point. These optimization techniques result in a translation from the input image to the reference image. The alignment manager 506 can then convert the determined translation into instructions to move the user device in space to achieve the desired alignment. This processing may be performed iteratively on subsequent frames until the reference points of the input image and the reference image are aligned. In some embodiments, the reference points are aligned when the determined translation has a magnitude below a threshold value.

Figure 6:
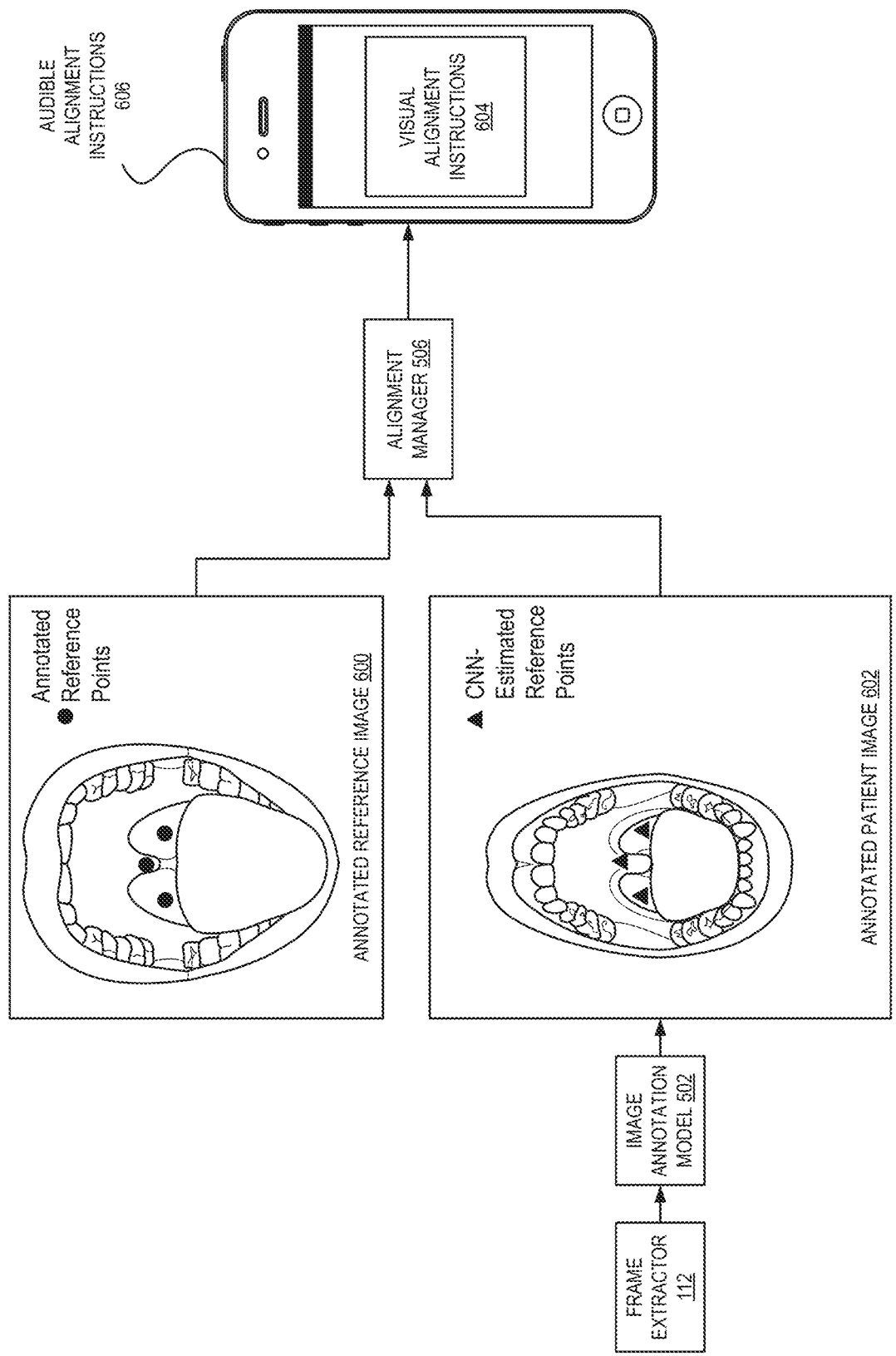
FIG. 6 is a diagram illustrating an example of reference point alignment according to some embodiments.

FIG. 6 is a diagram illustrating an example of reference point alignment according to some embodiments. As discussed, when an annotated reference image 600 is found to match the patient's image (e.g., using a classification model, described above), the patient's image is then annotated by image annotation model 502 to produce annotated patient image 602. This results in two annotated images to be compared by alignment manager 506. Alignment manager 506 then performs point set alignment on the annotated images to determine a translation needed to align the two sets of points (e.g., the reference points of reference image 600 and the annotated points of annotated patient image 602). This translation is then converted into alignment instructions to be provided to the patient, which instruct the patient to change the position and/or attitude of their user device to better align their image with the reference image.

As discussed, the alignment instructions may include visual alignment instructions 604, which indicate one or more directions in which to change the position and/or attitude of the user device. In the example of FIG. 6, the patient is capturing images of their throat using a smartphone. The screen is not readily viewable during such image capture, making visual alignment instructions largely useless. As such, embodiments may additionally, or alternatively, provide audible alignment instructions 606. In some embodiments, the audible alignment instructions express the same or similar instructions as would be shown visually, audibly (e.g., through a built-in speaker, wired or wireless headset, or other audio device coupled to the user device). In response to the instructions, the patient changes the position and/or attitude of their user device and the process repeats. As discussed, the user device may capture continuous video which is analyzed by the client application. As such, a frame is extracted subsequent to the alignment instructions being provided. This new frame is then similarly annotated with estimated reference points and compared to the reference points of the reference image. If the images are now aligned, then the process completes and the aligned image is captured and analyzed, as discussed above. If the images are still not aligned, then new alignment instructions are provided, and the process continues until alignment is achieved.

In some embodiments, there is a cool down period after the alignment instructions are provided. For example, there is typically not significant change from one frame to the next. If new instructions are provided for each frame, the patient will be provided with many repetitive instructions, which would result in a poor user experience. As such, after the instruction has been provided, the client application may wait a set number of frames until analysis is performed again. The number of cooldown frames may depend on the framerate of the video being captured. For example, if the framerate is 30 fps, then the cooldown might be in the range of 5-15 frames. Alternatively, the alignment instructions may be determined continuously for each frame and the visual or audible instructions updated accordingly.

Figure 7:
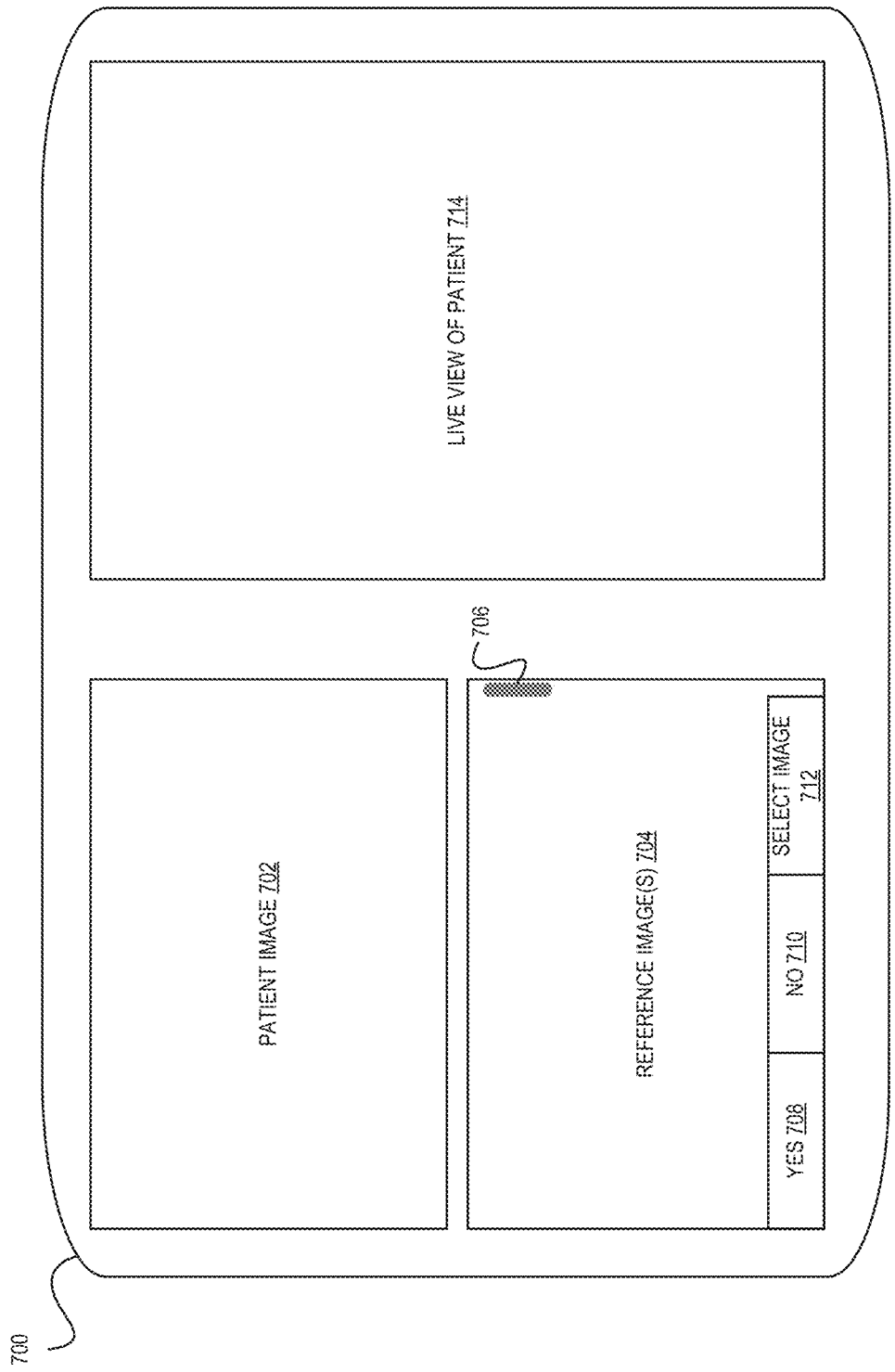
FIG. 7 is a diagram illustrating a provider user interface according to some embodiments.

FIG. 7 is a diagram illustrating a provider user interface according to some embodiments. As shown in FIG. 7, agent device 700 can include a screen or other display device which is capable of rendering a user interface provided by client application 104B. In various embodiments, the user interface may include a patient image 702. The patient image may include the aligned image that was captured by the patient in response to the alignment instructions provided above. As discussed, the patient image may be provided from the user device to the agent device via telemedicine service 117. Additionally, the user interface may include one or more reference images 704. This can include a ranked list of reference images which were most likely to match the patient image 702, and which the provider may browse by interacting with the user interface, such as via scroll element 706.

In some embodiments, as the provider browses the reference images 704, they can indicate whether the reference image is likely a match for the patient image 702, by selecting yes 708 or no 710. These options may be variously represented (e.g., as a checkmark and X, or other indication). In some embodiments, the reference images may be reranked based on the provider feedback. For example, if the provider indicates that it does not match a rash reference image, then the other rashes may be moved lower in their ranks. Once the provider has identified a likely match and selected yes 708, the client application 104B can provide other information to the provider for diagnostic aid purposes, such as a diagnostic code associated with the condition, treatment information, etc.

In some embodiments, the provider may select a specific reference image they want to compare the patient image to rather than the image(s) selected by the machine learning model. For example, if the patient's ailment was previously treated, the provider may wish to compare the current state of the ailment to the prior state of the ailment. In such instances, the provider may choose the option to select image 712 and find the patient's image from a previous visit (e.g., a HIPAA-compliant data store that includes the patient's file, etc.). In some embodiments, the patient may then be instructed to capture a new image that is aligned with their previous image. As such, the patient's previous image is used as a reference image for the alignment processes, described above.

In a telemedicine setting, provider will be on a videoconference with the patient and will have a live view of the patient 714 on their monitor. In some embodiments, the patient image 702 and reference images 704 may be overlaid on the screen of the doctor so that it either wholly, or in-part, obstructs the view of the patient's video 714 so that the doctor can examine the ailment at length while communicating eye-to-eye with the patient.

In some embodiments, the provider may provide manual instructions for aligning the patient's device with the ailment. The provider may dictate movements to the patient to get them to align their phone properly. For instance, the doctor might push the left/right/up/down arrow keys and a message is sent to the patient's phone which indicates that the phone is to be moved in the corresponding direction.

Figure 8:
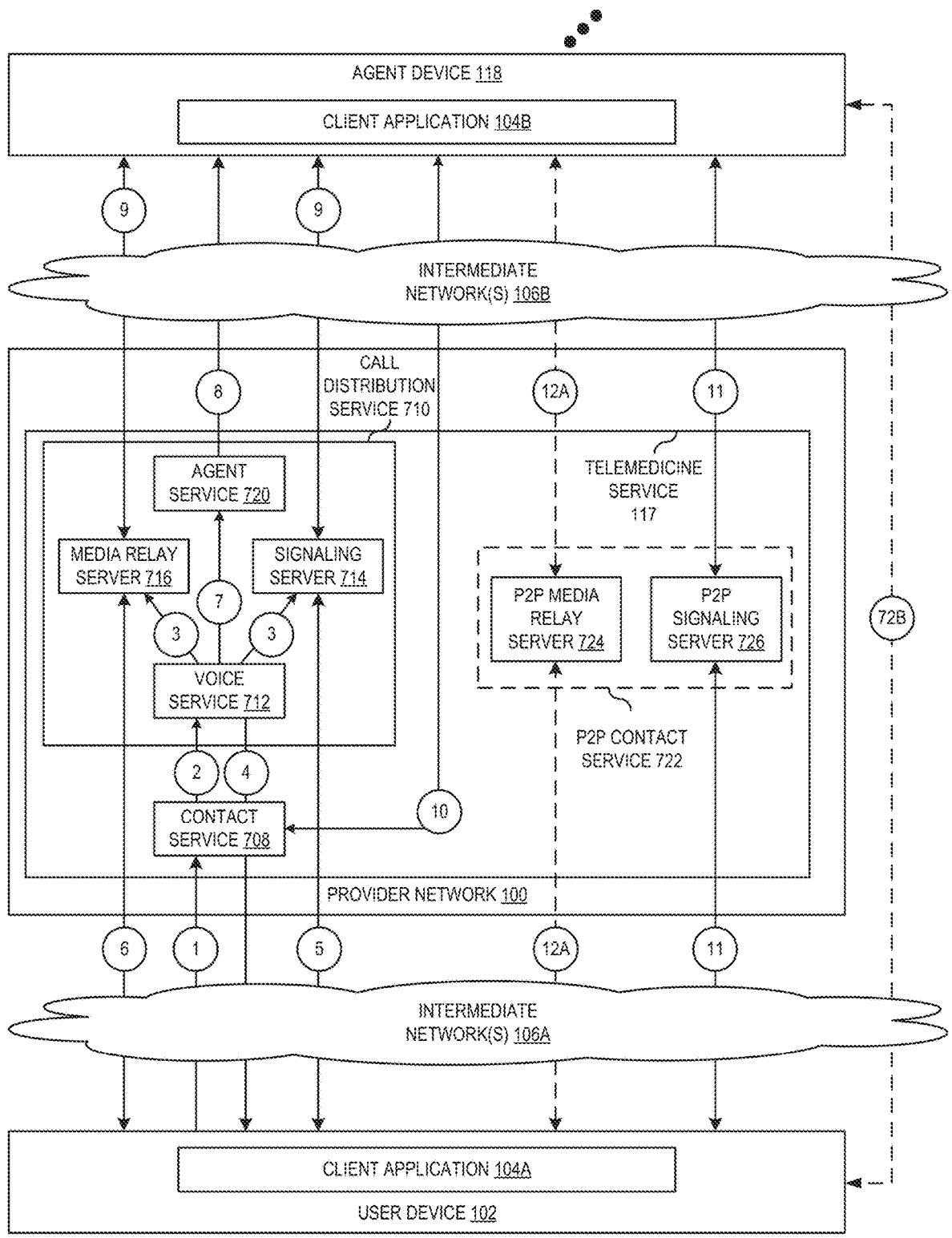
FIG. 8 is a diagram illustrating an environment for a telemedicine service according to some embodiments.

FIG. 8 is a diagram illustrating an environment for a telemedicine service according to some embodiments. As shown in FIG. 8, a user device 102, such as a phone, tablet, laptop computer, desktop computer, or other computing device, can include a client application 104A. The client application 104A may include a web browser, teleconferencing application, telemedicine application, or other application executing thereon, through which a user may contact an agent. Although embodiments are described with respect to telemedicine providers, embodiments may be implemented in various teleconferencing domains. Using the client application 104A, the user may request to be connected with a telemedicine provider (or other agent). The client application, at numeral 1, can send a request to a contact service 808 over intermediate network(s) 106A (e.g., the interna). In various embodiments, the request may be made using one or more application programming interfaces (APIs), such as a representational state transfer (REST) API, or other web services API. Contact service 808 may serve as an interface between user devices and a call distribution service 810 implemented in provider network 100. In some embodiments, contact service 808 can determine whether a particular call is to be connected using both the P2P connection and the call distribution service connection, or only through the call distribution service connection.

After receiving a request to initiate a new call at numeral 1, contact service 808 can send a request to voice service 812 of call distribution service 810. Voice service 812 may be accessible via an API gateway or other endpoint. In some embodiments, the voice service 812 can authenticate the request to initiate a new call. For example, the request may include credentials provided by the client application 104A in the initial request sent to contact service 808. In some embodiments, the request may be authenticated prior to it being received by voice service 812. Once authenticated, voice service 812 can then perform call configuration. In some embodiments, WebRTC may be used for media connections. WebRTC enables web browsers to exchange media in real time. For example, video calls may be made between web browsers using WebRTC. The voice service 812, at numeral 3, can configure signaling server(s) 814 and, depending on implementation, session traversal utilities for network address translation (STUN) server(s) or traversal using relay network address translation (TURN) server(s) 816. Signaling servers 814 enable the client application 104A on user device 102 to exchange session description protocol (SDP) with an agent to establish a call via a media relay server 816, such as a TURN server. The SDP can define call requirements of the user device, such as codec requirements, network details, device details, and other data needed to establish a call session such as encryption keys. Both the client application 104A on user device 102, and a client device 104B on the agent device 118 may provide an SDP to signaling server 814 which may then identify a media relay server 816 that meets the technical requirements of both parties to the call. In some embodiments, multiple candidate servers may be provided.

At numeral 4, references to the signaling server(s) and media relay server(s) can be returned to the client application 104A on user device 102. The references may include URLs, URIs, or other endpoint data that enables the client application to connect to the signaling server(s) and media relay server(s). At numeral 5, the client application 104A can provide its SDP to the signaling server 814. At numeral 6, the client application 104A can connect to the media relay server and perform address discovery, for example using the interactive connectivity establishment (ICE) framework provided by WebRTC. This establishes the user-side of the call. In response, at numeral 7, the voice service 812 can send a request to agent service 820 to identify an available provider. At numeral 8, the agent service can provide the endpoint data for the signaling server and media relay server to the available provider's client application 104B executing on agent device 118.

In some embodiments, an identifier associated with the user can be provided to the provider at numeral 8 along with the endpoint data for call distribution service 810. The identifier may be a token associated with the user which may be used by the provider to obtain information about the user. The identifier may be tokenized to prevent identifiable information about the call session being established from being intercepted. The identifier may itself be sensitive information, as such the token may be a representation of the identifier that maps to the identifier. For example, the token may be used to retrieve a medical file associated with the user. The provider can determine whether to accept the call based on the information about the user retrieved using the identifier. The provider, such as a doctor, nurse, or other telemedicine provider, can accept the call through client application 104B and the client application can connect, at numeral 9, to the signaling server 814 and media relay server 816 using the endpoint data received from the agent service 820.

The process described above with respect to numerals 1-9 establishes a first connection between a user and an agent. The media relay server can be used to transfer the audio and video data of the teleconference. However, this can lead to reduced performance due to limited bandwidth availability through the call distribution service and the longer network path between the user and the provider. Additionally, such a connection routes the content of the teleconference through the servers of the call distribution service. Depending on the content being transferred, this may require additional security be applied to the transfer that the call distribution service is not configured to provide. As such, embodiments provide a second connection via a peer to peer (P2P) contact service 822 for the media stream.

In some embodiments, when a call is accepted by the provider, a contact identifier (e.g., a session token, call type, or other identifier) associated with the session may be sent to the provider and the user by the signaling server 814. At numeral 10, the agent device can use the contact identifier to request endpoint data associated with a P2P contact service 822. In some embodiments, the contact service may also provide endpoint data associated with the P2P contact service to the user. The P2P endpoint data may include address information for one or more P2P media relay servers 824 and one or more P2P signaling servers 826. In some embodiments, the P2P media relay servers and P2P signaling servers may be owned by separate services, maintained in separate private networks, or otherwise provided separately. This may be used to improve security. For example, encryption keys may be provided to the agent device and the user device via P2P signaling server 826 and then used to open a secure connection using P2P media relay server 824. In some embodiments, the encryption techniques used may be selected to meet standards for handling personal health information (PHI) securely, such as Advanced Encryption Standard (AES) 128, 192 or 256-bit encryption, OpenPGP, S/MIME, etc. If the P2P signaling server and the P2P media relay server are implemented as separate services, then if one were to be compromised personal health information (PHI) would not be exposed (e.g., if the signaling server is compromised the keys could be exposed but there is no media flowing through the signaling server to be decrypted, likewise if the P2P media relay server were compromised the keys would secure with the signaling server and could not be used to decrypt the media stream). This reduces the risk of PHI being intercepted by a man-in-the-middle attack, or other attack while the data is in flight between the agent device and the user device.

At numeral 11, the agent device and the user device may each connect to the P2P signaling server 826 based on the endpoint data. Using the contact identifier associated with the P2P session, each peer can identify one another and perform WebRTC address discovery using the candidate media relay server(s) 824. The media relay servers 824 may include STUN servers that facilitate direct P2P connections between the peers or TURN servers that act as a relay between the peers, depending on the network configuration of each peer. An SDP offer can then be constructed and sent via the P2P signaling server directly to the other peer. Using the SDP, P2P media stream (e.g., audio and video streams) can be established which are shown and played on each client application 104A and 104B. Depending on network topology, the P2P media stream can be established via P2P media relay server 824 (e.g., a TURN server), as shown at 12A, or the P2P media stream may be established directly between the agent device and client device based on routing information obtained from the P2P media relay server 824 (e.g., a STUN server), as shown at 12B.

Once the P2P media streams are established, the teleconference is in progress between the user and the provider. In addition to the media streams which are shown and played on their respective devices via the P2P connection, a second audio stream is additionally provided to the call distribution service 810 via the open connection to media relay server(s) 816. This second audio stream is used by the call distribution service 810 to perform transcription, collect metrics (e.g., call duration, provider availability, user wait time, etc.), and/or other data about the connection. In some embodiments, audio data from the second audio stream may be sent to each client application 104A and 104B, however this audio may be ignored by each device. As a result, only the media received via the P2P connection is displayed/played on each device. In some embodiments, audio may only be sent to the call distribution service 810 from each device, and the call distribution service 810 does not provide audio data to either device. This may reduce the bandwidth required associated with the second audio connection.

In some embodiments, call distribution service 810 can transcribe the second audio stream in real time. The audio data may be transcribed using a variety of automatic speech recognition (ASR) techniques, including Speech to Text, Hidden Markov models, machine learning techniques, etc. This may assist the provider with potential diagnoses, provide questions to ask during the call, and prepare notes about the call that are ready when the call is complete. In some embodiments, the second audio stream may be used to provide real-time translation of the audio stream. The translated audio data may be presented to the provider and user either through captions or a separate audio feed (e.g., text to speech).

In some embodiments, additional data may be shared over the P2P connection via the P2P media relay server(s) 824. For example, screenshots and/or photos may be obtained from the user device. The user device may include a camera which the user can position over an area of interest (e.g., a wound, rash, or other medical condition that is visible on their person). The user can capture an image of the area of interest and the image is sent over the P2P media connection to the provider. Additionally, or alternatively, the provide may send a capture command to the user device via the P2P signaling server (726) which causes the user device 102 to capture image data and send the image data to the provider over the P2P media connection. This keeps any potentially sensitive data, such as health information, separate from the routing information.

In some embodiments, the user device 102 and/or the agent device 118 may include a plurality of input devices that can capture media to be transmitted over the P2P media connection. For example, an agent device may include a throat camera, ear camera, etc. that can capture images of a patient. The client application 104A, 104B can be used to select the input device that is used to provide media data over the P2P media connection, enabling the user and/or provider to swap between different input devices.

Figure 9:
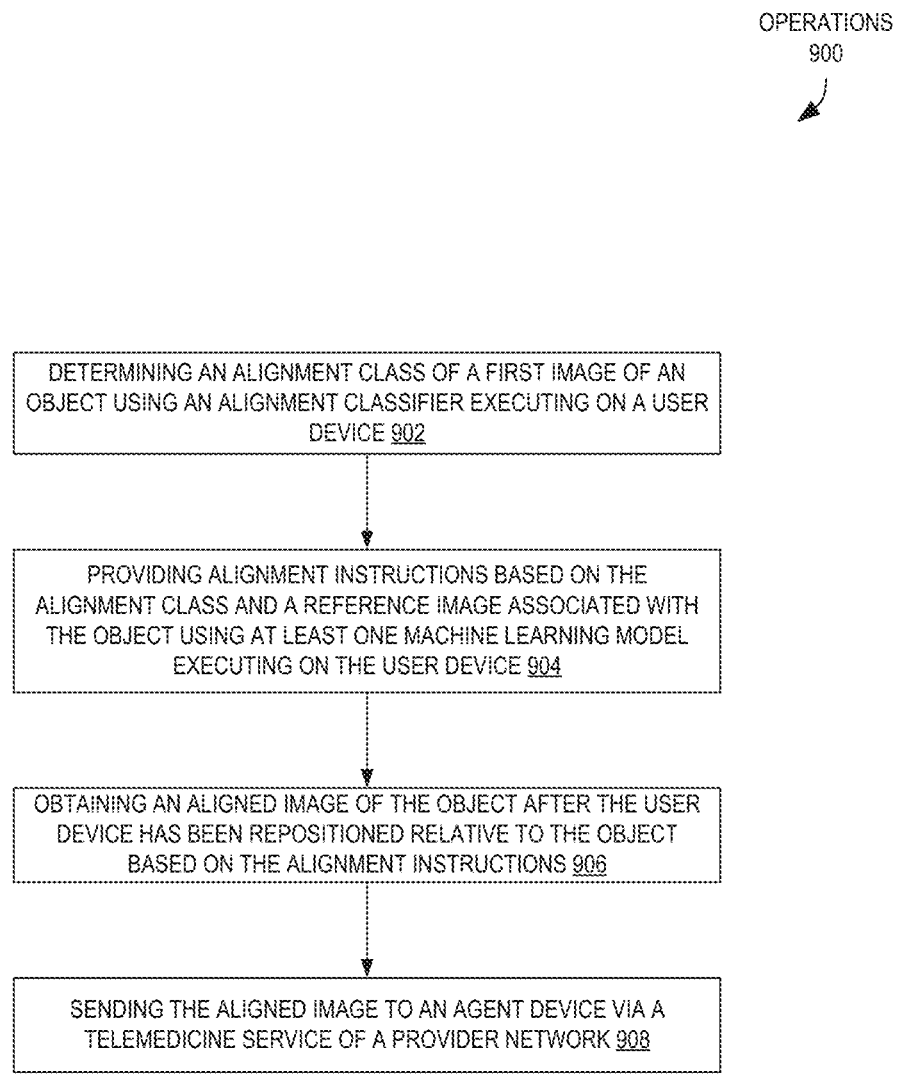
FIG. 9 is a flow diagram illustrating operations of a method for automated alignment of image capture of physical ailments according to some embodiments.

FIG. 9 is a flow diagram illustrating operations 900 of a method for automated alignment of image capture of physical ailments according to some embodiments. Some or all of the operations 900 (or other processes described herein, or variations, and/or combinations thereof) are performed under the control of one or more computer systems configured with executable instructions, and are implemented as code (e.g., executable instructions, one or more computer programs, or one or more applications) executing collectively on one or more processors. The code is stored on a computer-readable storage medium, for example, in the form of a computer program comprising instructions executable by one or more processors. The computer-readable storage medium is non-transitory. In some embodiments, one or more (or all) of the operations 900 are performed by client application 104A or 104B, telemedicine service 117, or other components of the other figures.

The operations 900 include, at block 902, determining an alignment class of a first image of an object using an alignment classifier executing on a user device. As discussed, in some embodiments, some ailments are located such that alignment can be performed using surface normals of the ailment and the user device. However, other ailments are located where such alignment is impractical, and instead a reference point alignment is performed. In some embodiments, determining an alignment class includes determining the reference image most likely to match the object depicted in the first image, and determining an alignment type associated with the reference image.

The operations 900 further include, at block 904, providing alignment instructions based on the alignment class and a reference image associated with the object using at least one machine learning model executing on the user device. In some embodiments, when the alignment type is a normal alignment, providing the alignment instructions further includes determining a second surface normal associated with the user device, determining a center of mass difference vector between the object and the user device, and generating the alignment instructions to align the user device and the object based at least on the first surface normal, the second surface normal, and the center of mass difference vector. In some embodiments, generating the alignment instructions includes generating a first alignment instruction to change a position of the user device such that a dot product of the first surface normal and the center of mass difference vector is approximately equal to 1, and generating a second alignment instruction to change an attitude of the user device such that a dot product of the first surface normal and the second surface normal is approximately equal to −1.

In some embodiments, determining a first surface normal associated with the object, further includes determining a location associated with the object using a localization model, wherein the object is a medical ailment visible on a body part of a patient, and wherein the localization model is a neural network trained to identify ailments in image data, determining an alignment model of the body part of the patient using an alignment model, wherein the alignment model is a neural network trained to generate a geometric representation of a body part in image data, and determining the first surface at the location associated with the object based on the geometric representation of the body part.

The operations 900 further include, at block 906, obtaining an aligned image of the object after the user device has been repositioned relative to the object based on the alignment instructions. For example, the aligned image may be a frame extracted from a video captured by the camera and determined to be aligned with the ailment based on the techniques described herein. In some embodiments, the operations further include capturing video data using a camera coupled to a user device, wherein the first image of the object is a first frame of the video data and wherein the aligned image of the object is a second frame of the video data.

In some embodiments, when the alignment type is determined to be reference point alignment, providing the alignment instructions includes estimating a first plurality of reference points associated with the first image using an image annotation model, identifying a second plurality of reference points associated with the reference image, determining a translation between the first plurality of reference points and the second plurality of reference points based on point set alignment, and generating the alignment instructions based at least on the translation. In some embodiments, the alignment instructions are displayed via the user device or reproduced audibly via the user device.

The operations 900 further include, at block 908, sending the aligned image to an agent device via a telemedicine service of a provider network. In some embodiments, sending the aligned image includes sending ranks associated with a plurality of reference images to the agent device, wherein each rank indicates a likelihood of a match between the aligned image and a corresponding reference image, wherein the agent device displays the aligned image and at least one of the reference images to a provider for review.

In some embodiments, the method includes obtaining a first image of an ailment using a camera coupled to a mobile device, determining an alignment class of the first image of the ailment using an alignment classifier executing on the mobile device, generating alignment instructions based on the alignment class and a reference image associated with the ailment using at least one machine learning model executing on the mobile device, providing the alignment instructions via the mobile device, obtaining a second image of the ailment using the camera after the mobile device has been repositioned relative to the ailment based on the alignment instructions, determining the second image of the ailment is aligned with the reference image, and sending the second image to an agent device via a telemedicine service of a provider network. In some embodiments, the alignment instructions indicate a change in position or attitude of the mobile device. In some embodiments, the method further includes sending a request to the telemedicine service to initiate a session with a provider, wherein the telemedicine service identifies an available provider associated with the agent device and enables a secure connection to be established between the mobile device and the agent device.

Figure 10:
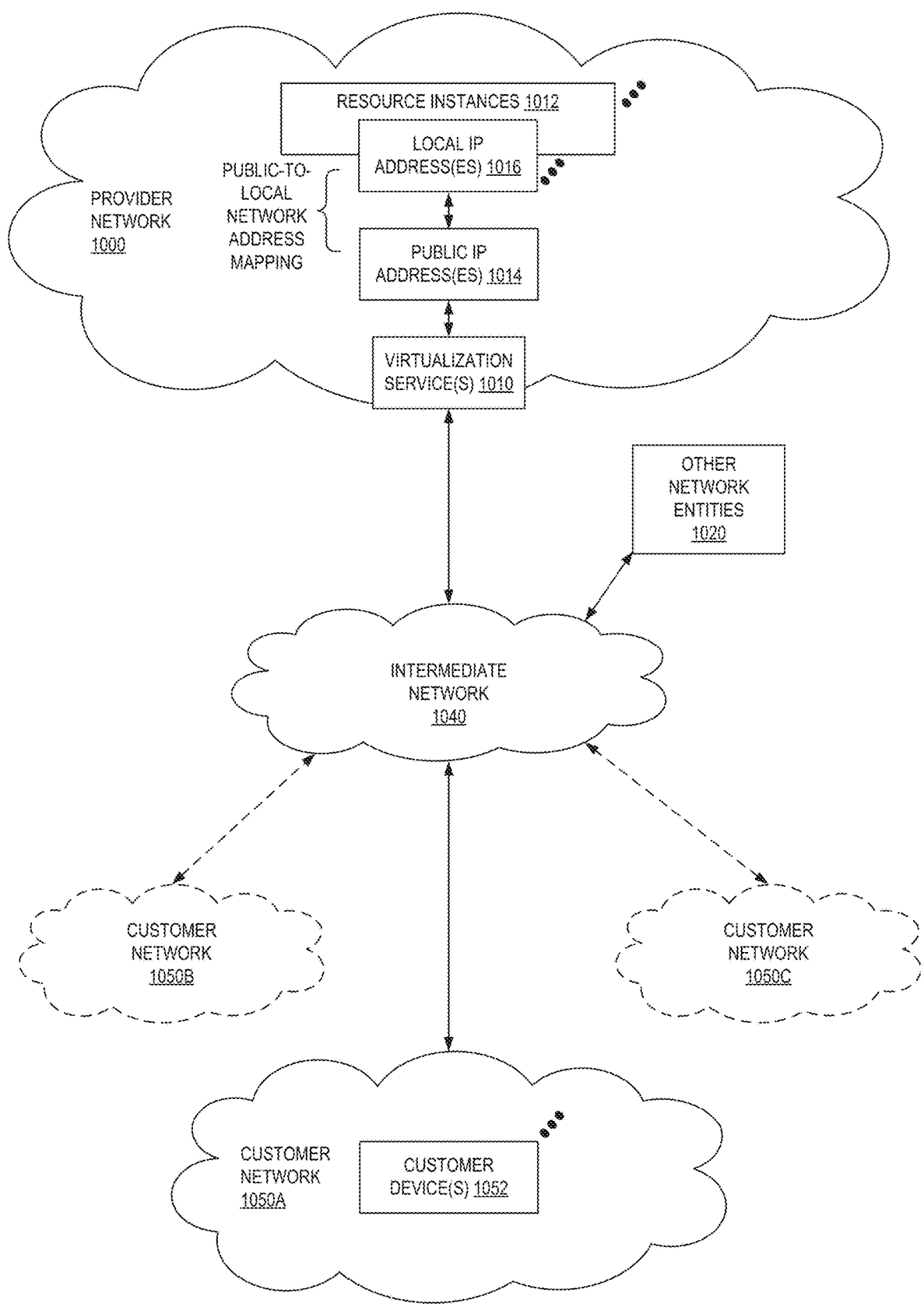
FIG. 10 illustrates an example provider network environment according to some embodiments.

FIG. 10 illustrates an example provider network (or "service provider system") environment according to some embodiments. A provider network 1000 can provide resource virtualization to customers via one or more virtualization services 1010 that allow customers to purchase, rent, or otherwise obtain instances 1012 of virtualized resources, including but not limited to computation and storage resources, implemented on devices within the provider network or networks in one or more data centers. Local Internet Protocol (IP) addresses 1016 can be associated with the resource instances 1012; the local IP addresses are the internal network addresses of the resource instances 1012 on the provider network 1000. In some embodiments, the provider network 1000 can also provide public IP addresses 1014 and/or public IP address ranges (e.g., Internet Protocol version 4 (IPv4) or Internet Protocol version 6 (IPv6) addresses) that customers can obtain from the provider 1000.

Conventionally, the provider network 1000, via the virtualization services 1010, can allow a customer of the service provider (e.g., a customer that operates one or more customer networks 1050A-1050C (or "client networks") including one or more customer device(s) 1052) to dynamically associate at least some public IP addresses 1014 assigned or allocated to the customer with particular resource instances 1012 assigned to the customer. The provider network 1000 can also allow the customer to remap a public IP address 1014, previously mapped to one virtualized computing resource instance 1012 allocated to the customer, to another virtualized computing resource instance 1012 that is also allocated to the customer. Using the virtualized computing resource instances 1012 and public IP addresses 1014 provided by the service provider, a customer of the service provider such as the operator of the customer network(s) 1050A-1050C can, for example, implement customer-specific applications and present the customer's applications on an intermediate network 1040, such as the Internet. Other network entities 1020 on the intermediate network 1040 can then generate traffic to a destination public IP address 1014 published by the customer network(s) 1050A-1050C; the traffic is routed to the service provider data center, and at the data center is routed, via a network substrate, to the local IP address 1016 of the virtualized computing resource instance 1012 currently mapped to the destination public IP address 1014. Similarly, response traffic from the virtualized computing resource instance 1012 can be routed via the network substrate back onto the intermediate network 1040 to the source entity 1020.

Local IP addresses, as used herein, refer to the internal or "private" network addresses, for example, of resource instances in a provider network. Local IP addresses can be within address blocks reserved by Internet Engineering Task Force (IETF) Request for Comments (RFC) 1918 and/or of an address format specified by IETF RFC 4193 and can be mutable within the provider network. Network traffic originating outside the provider network is not directly routed to local IP addresses; instead, the traffic uses public IP addresses that are mapped to the local IP addresses of the resource instances. The provider network can include networking devices or appliances that provide network address translation (NAT) or similar functionality to perform the mapping from public IP addresses to local IP addresses and vice versa.

Public IP addresses are Internet mutable network addresses that are assigned to resource instances, either by the service provider or by the customer. Traffic routed to a public IP address is translated, for example via 1:1 NAT, and forwarded to the respective local IP address of a resource instance.

Some public IP addresses can be assigned by the provider network infrastructure to particular resource instances; these public IP addresses can be referred to as standard public IP addresses, or simply standard IP addresses. In some embodiments, the mapping of a standard IP address to a local IP address of a resource instance is the default launch configuration for all resource instance types.

At least some public IP addresses can be allocated to or obtained by customers of the provider network 1000; a customer can then assign their allocated public IP addresses to particular resource instances allocated to the customer. These public IP addresses can be referred to as customer public IP addresses, or simply customer IP addresses. Instead of being assigned by the provider network 1000 to resource instances as in the case of standard IP addresses, customer IP addresses can be assigned to resource instances by the customers, for example via an API provided by the service provider. Unlike standard IP addresses, customer IP addresses are allocated to customer accounts and can be remapped to other resource instances by the respective customers as necessary or desired. A customer IP address is associated with a customer's account, not a particular resource instance, and the customer controls that IP address until the customer chooses to release it. Unlike conventional static IP addresses, customer IP addresses allow the customer to mask resource instance or availability zone failures by remapping the customer's public IP addresses to any resource instance associated with the customer's account. The customer IP addresses, for example, enable a customer to engineer around problems with the customer's resource instances or software by remapping customer IP addresses to replacement resource instances.

Figure 11:
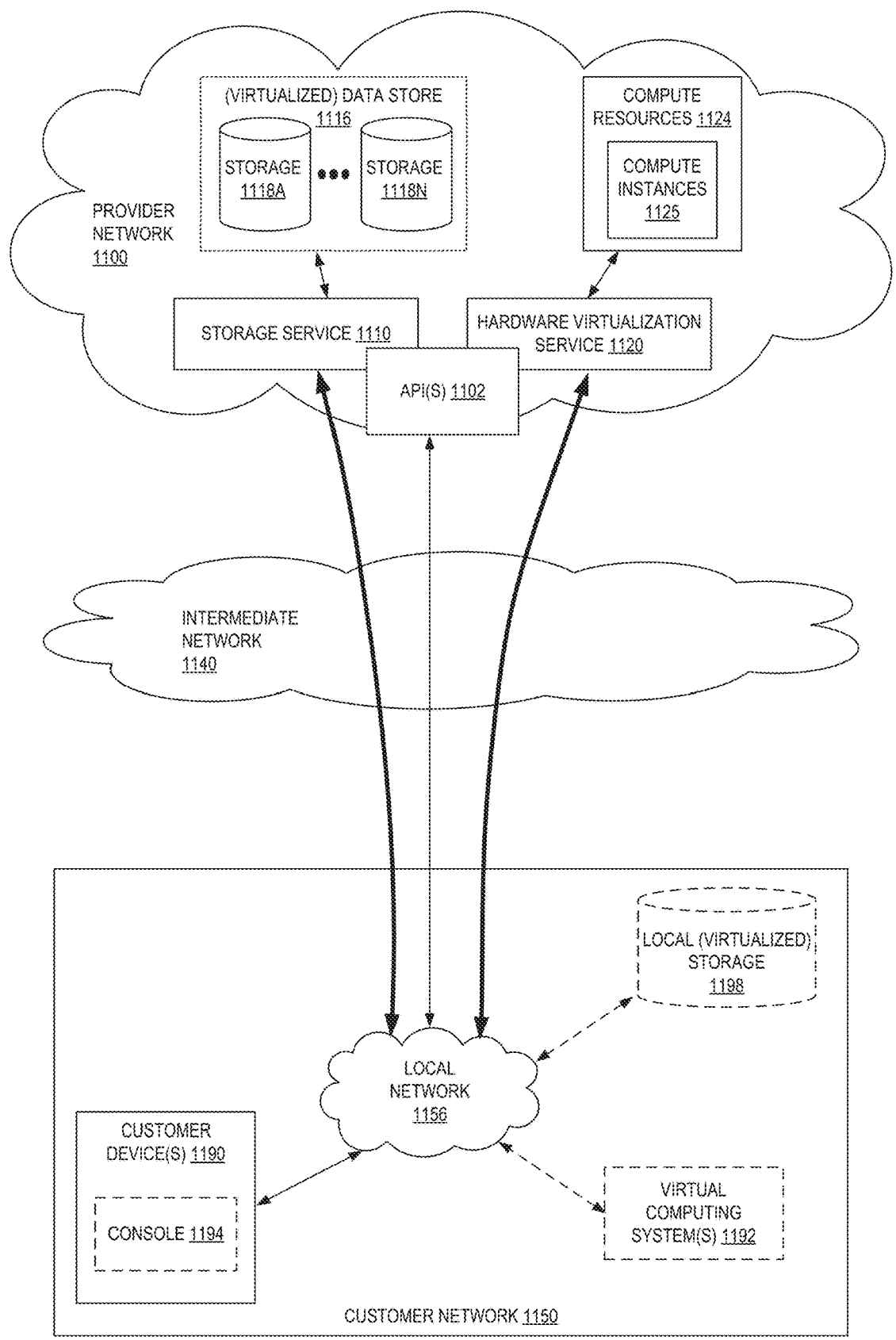
FIG. 11 is a block diagram of an example provider network that provides a storage service and a hardware virtualization service to customers according to some embodiments.

FIG. 11 is a block diagram of an example provider network environment that provides a storage service and a hardware virtualization service to customers, according to some embodiments. A hardware virtualization service 1120 provides multiple compute resources 1124 (e.g., compute instances 1125, such as VMs) to customers. The compute resources 1124 can, for example, be provided as a service to customers of a provider network 1100 (e.g., to a customer that implements a customer network 1150). Each computation resource 1124 can be provided with one or more local IP addresses. The provider network 1100 can be configured to route packets from the local IP addresses of the compute resources 1124 to public Internet destinations, and from public Internet sources to the local IP addresses of the compute resources 1124.

The provider network 1100 can provide the customer network 1150, for example coupled to an intermediate network 1140 via a local network 1156, the ability to implement virtual computing systems 1192 via the hardware virtualization service 1120 coupled to the intermediate network 1140 and to the provider network 1100. In some embodiments, the hardware virtualization service 1120 can provide one or more APIs 1102, for example a web services interface, via which the customer network 1150 can access functionality provided by the hardware virtualization service 1120, for example via a console 1194 (e.g., a web-based application, standalone application, mobile application, etc.) of a customer device 1190. In some embodiments, at the provider network 1100, each virtual computing system 1192 at the customer network 1150 can correspond to a computation resource 1124 that is leased, rented, or otherwise provided to the customer network 1150.

From an instance of the virtual computing system(s) 1192 and/or another customer device 1190 (e.g., via console 1194), the customer can access the functionality of a storage service 1110, for example via the one or more APIs 1102, to access data from and store data to storage resources 1118A-1118N of a virtual data store 1116 (e.g., a folder or "bucket," a virtualized volume, a database, etc.) provided by the provider network 1100. In some embodiments, a virtualized data store gateway (not shown) can be provided at the customer network 1150 that can locally cache at least some data, for example frequently accessed or critical data, and that can communicate with the storage service 1110 via one or more communications channels to upload new or modified data from a local cache so that the primary store of data (the virtualized data store 1116) is maintained. In some embodiments, a user, via the virtual computing system 1192 and/or another customer device 1190, can mount and access virtual data store 1116 volumes via the storage service 1110 acting as a storage virtualization service, and these volumes can appear to the user as local (virtualized) storage 1198.

While not shown in FIG. 11, the virtualization service(s) can also be accessed from resource instances within the provider network 1100 via the API(s) 1102. For example, a customer, appliance service provider, or other entity can access a virtualization service from within a respective virtual network on the provider network 1100 via the API(s) 1102 to request allocation of one or more resource instances within the virtual network or within another virtual network.

Illustrative Systems

Figure 12:
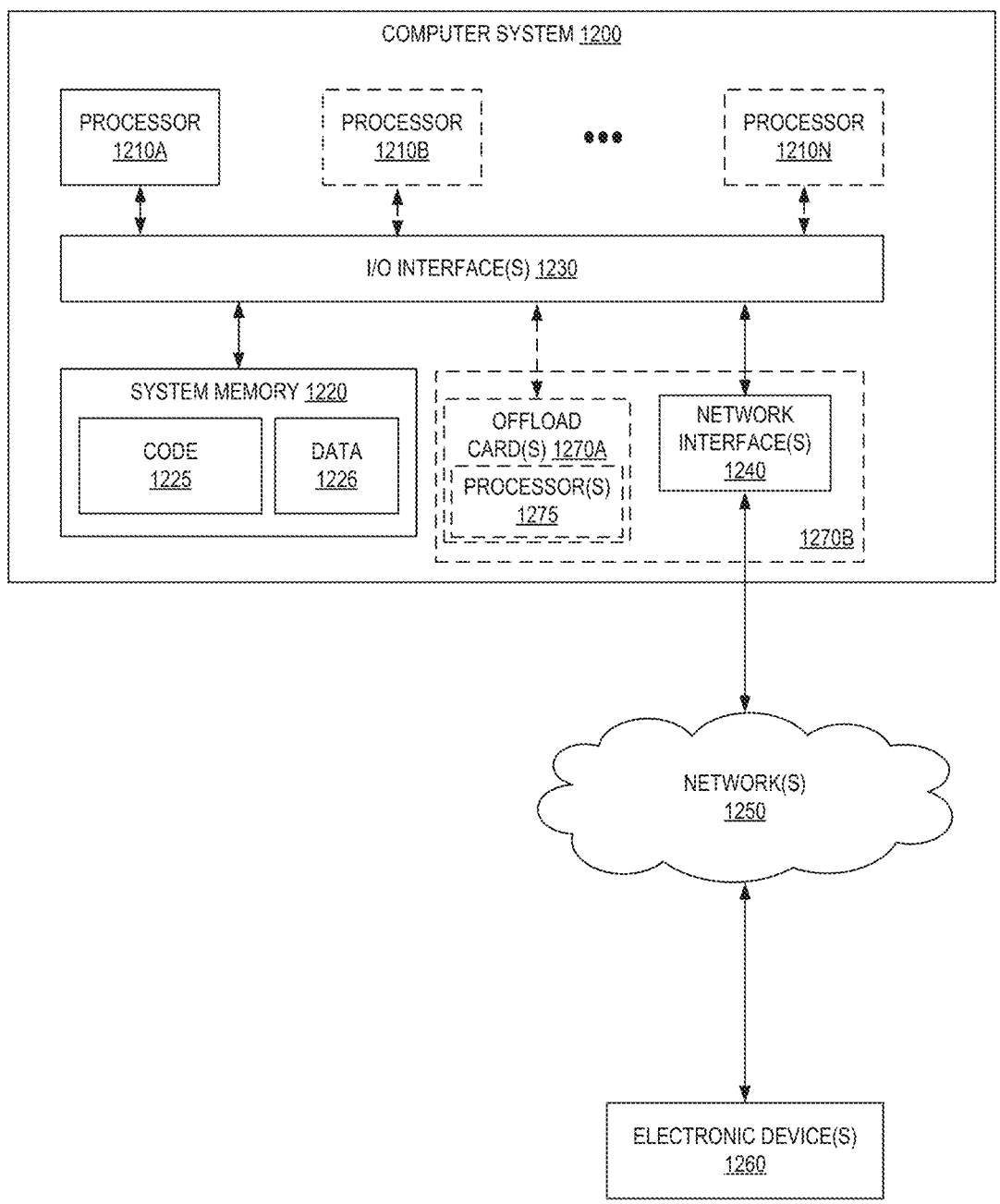
FIG. 12 is a block diagram illustrating an example computer system that can be used in some embodiments.

In some embodiments, a system that implements a portion or all of the techniques described herein can include a general-purpose computer system, such as the computer system 1200 illustrated in FIG. 12, that includes, or is configured to access, one or more computer-accessible media. In the illustrated embodiment, the computer system 1200 includes one or more processors 1210 coupled to a system memory 1220 via an input/output (I/O) interface 1230. The computer system 1200 further includes a network interface 1240 coupled to the I/O interface 1230. While FIG. 12 shows the computer system 1200 as a single computing device, in various embodiments the computer system 1200 can include one computing device or any number of computing devices configured to work together as a single computer system 1200.

In various embodiments, the computer system 1200 can be a uniprocessor system including one processor 1210, or a multiprocessor system including several processors 1210 (e.g., two, four, eight, or another suitable number). The processor(s) 1210 can be any suitable processor(s) capable of executing instructions. For example, in various embodiments, the processor(s) 1210 can be general-purpose or embedded processors implementing any of a variety of instruction set architectures (ISAs), such as the x86, ARM, PowerPC, SPARC, or MIPS ISAs, or any other suitable ISA. In multiprocessor systems, each of the processors 1210 can commonly, but not necessarily, implement the same ISA.

The system memory 1220 can store instructions and data accessible by the processor(s) 1210. In various embodiments, the system memory 1220 can be implemented using any suitable memory technology, such as random-access memory (RAM), static RAM (SRAM), synchronous dynamic RAM (SDRAM), nonvolatile/Flash-type memory, or any other type of memory. In the illustrated embodiment, program instructions and data implementing one or more desired functions, such as those methods, techniques, and data described above, are shown stored within the system memory 1220 as code 1225 (e.g., executable to implement, in whole or in part, the telemedicine service 117, client application 104A, 104B, or other service or application as described herein) and data 1226.

In some embodiments, the I/O interface 1230 can be configured to coordinate I/O traffic between the processor 1210, the system memory 1220, and any peripheral devices in the device, including the network interface 1240 and/or other peripheral interfaces (not shown). In some embodiments, the I/O interface 1230 can perform any necessary protocol, timing, or other data transformations to convert data signals from one component (e.g., the system memory 1220) into a format suitable for use by another component (e.g., the processor 1210). In some embodiments, the I/O interface 1230 can include support for devices attached through various types of peripheral buses, such as a variant of the Peripheral Component Interconnect (PCI) bus standard or the Universal Serial Bus (USB) standard, for example. In some embodiments, the function of the I/O interface 1230 can be split into two or more separate components, such as a north bridge and a south bridge, for example. Also, in some embodiments, some or all of the functionality of the I/O interface 1230, such as an interface to the system memory 1220, can be incorporated directly into the processor 1210.

The network interface 1240 can be configured to allow data to be exchanged between the computer system 1200 and other devices 1260 attached to a network or networks 1250, such as other computer systems or devices as illustrated in FIG. 1, for example. In various embodiments, the network interface 1240 can support communication via any suitable wired or wireless general data networks, such as types of Ethernet network, for example. Additionally, the network interface 1240 can support communication via telecommunications/telephony networks, such as analog voice networks or digital fiber communications networks, via storage area networks (SANs), such as Fibre Channel SANs, and/or via any other suitable type of network and/or protocol.

In some embodiments, the computer system 1200 includes one or more offload cards 1270A or 1270B (including one or more processors 1275, and possibly including the one or more network interfaces 1240) that are connected using the I/O interface 1230 (e.g., a bus implementing a version of the Peripheral Component Interconnect—Express (PCI-E) standard, or another interconnect such as a QuickPath interconnect (QPI) or UltraPath interconnect (UPI)). For example, in some embodiments the computer system 1200 can act as a host electronic device (e.g., operating as part of a hardware virtualization service) that hosts compute resources such as compute instances, and the one or more offload cards 1270A or 1270B execute a virtualization manager that can manage compute instances that execute on the host electronic device. As an example, in some embodiments the offload card(s) 1270A or 1270B can perform compute instance management operations, such as pausing and/or un-pausing compute instances, launching and/or terminating compute instances, performing memory transfer/copying operations, etc. These management operations can, in some embodiments, be performed by the offload card(s) 1270A or 1270B in coordination with a hypervisor (e.g., upon a request from a hypervisor) that is executed by the other processors 1210A-1210N of the computer system 1200. However, in some embodiments the virtualization manager implemented by the offload card(s) 1270A or 1270B can accommodate requests from other entities (e.g., from compute instances themselves), and cannot coordinate with (or service) any separate hypervisor.

In some embodiments, the system memory 1220 can be one embodiment of a computer-accessible medium configured to store program instructions and data as described above. However, in other embodiments, program instructions and/or data can be received, sent, or stored upon different types of computer-accessible media. Generally speaking, a computer-accessible medium can include any non-transitory storage media or memory media such as magnetic or optical media, e.g., disk or DVD/CD coupled to the computer system 1200 via the I/O interface 1230. A non-transitory computer-accessible storage medium can also include any volatile or non-volatile media such as RAM (e.g., SDRAM, double data rate (DDR) SDRAM, SRAM, etc.), read only memory (ROM), etc., that can be included in some embodiments of the computer system 1200 as the system memory 1220 or another type of memory. Further, a computer-accessible medium can include transmission media or signals such as electrical, electromagnetic, or digital signals, conveyed via a communication medium such as a network and/or a wireless link, such as can be implemented via the network interface 1240.

Various embodiments discussed or suggested herein can be implemented in a wide variety of operating environments, which in some cases can include one or more user computers, computing devices, or processing devices which can be used to operate any of a number of applications. User or client devices can include any of a number of general-purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially available operating systems and other known applications for purposes such as development and database management. These devices also can include other electronic devices, such as dummy terminals, thin-clients, gaming systems, and/or other devices capable of communicating via a network.

Most embodiments use at least one network that would be familiar to those skilled in the art for supporting communications using any of a variety of widely available protocols, such as Transmission Control Protocol/Internet Protocol (TCP/IP), File Transfer Protocol (FTP), Universal Plug and Play (UPnP), Network File System (NFS), Common Internet File System (CIFS), Extensible Messaging and Presence Protocol (XMPP), AppleTalk, etc. The network(s) can include, for example, a local area network (LAN), a wide-area network (WAN), a virtual private network (VPN), the Internet, an intranet, an extranet, a public switched telephone network (PSTN), an infrared network, a wireless network, and any combination thereof.

In embodiments using a web server, the web server can run any of a variety of server or mid-tier applications, including HTTP servers, File Transfer Protocol (FTP) servers, Common Gateway Interface (CGI) servers, data servers, Java servers, business application servers, etc. The server(s) also can be capable of executing programs or scripts in response requests from user devices, such as by executing one or more Web applications that can be implemented as one or more scripts or programs written in any programming language, such as Java®, C, C# or C++, or any scripting language, such as Perl, Python, PHP, or TCL, as well as combinations thereof. The server(s) can also include database servers, including without limitation those commercially available from Oracle®, Microsoft®, Sybase®, IBM®, etc. The database servers can be relational or non-relational (e.g., "NoSQL"), distributed or non-distributed, etc.

Environments disclosed herein can include a variety of data stores and other memory and storage media as discussed above. These can reside in a variety of locations, such as on a storage medium local to (and/or resident in) one or more of the computers or remote from any or all of the computers across the network. In a particular set of embodiments, the information can reside in a storage-area network (SAN) familiar to those skilled in the art. Similarly, any necessary files for performing the functions attributed to the computers, servers, or other network devices can be stored locally and/or remotely, as appropriate. Where a system includes computerized devices, each such device can include hardware elements that can be electrically coupled via a bus, the elements including, for example, at least one central processing unit (CPU), at least one input device (e.g., a mouse, keyboard, controller, touch screen, or keypad), and/or at least one output device (e.g., a display device, printer, or speaker). Such a system can also include one or more storage devices, such as disk drives, optical storage devices, and solid-state storage devices such as random-access memory (RAM) or read-only memory (ROM), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate embodiments can have numerous variations from that described above. For example, customized hardware might also be used and/or particular elements might be implemented in hardware, software (including portable software, such as applets), or both. Further, connection to other computing devices such as network input/output devices can be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory (EEPROM), flash memory or other memory technology, Compact Disc-Read Only Memory (CD-ROM), Digital Versatile Disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

Figure 13:
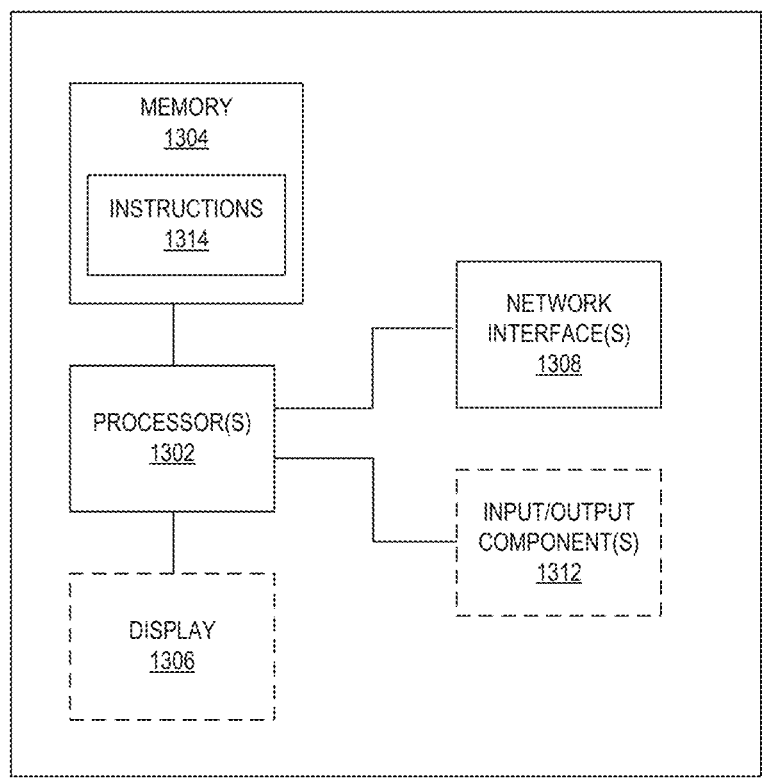
FIG. 13 illustrates a logical arrangement of a set of general components of an example computing device that can be used in accordance with various embodiments.

FIG. 13 illustrates a logical arrangement of a set of general components of an example computing device 1300 such as user device 102, agent device 118, etc. Generally, a computing device 1300 can also be referred to as an electronic device. The techniques shown in the figures and described herein can be implemented using code and data stored and executed on one or more electronic devices (e.g., a client end station and/or server end station). Such electronic devices store and communicate (internally and/or with other electronic devices over a network) code and data using computer-readable media, such as non-transitory computer-readable storage media (e.g., magnetic disks, optical disks, Random Access Memory (RAM), Read Only Memory (ROM), flash memory devices, phase-change memory) and transitory computer-readable communication media (e.g., electrical, optical, acoustical or other form of propagated signals, such as carrier waves, infrared signals, digital signals). In addition, such electronic devices include hardware, such as a set of one or more processors 1302 (e.g., wherein a processor is a microprocessor, controller, microcontroller, central processing unit, digital signal processor, application specific integrated circuit, field programmable gate array, other electronic circuitry, a combination of one or more of the preceding) coupled to one or more other components, e.g., one or more non-transitory machine-readable storage media (e.g., memory 1304) to store code (e.g., instructions 1314) and/or data, and a set of one or more wired or wireless network interfaces 1308 allowing the electronic device to transmit data to and receive data from other computing devices, typically across one or more networks (e.g., Local Area Networks (LANs), the Internet). The coupling of the set of processors and other components is typically through one or more interconnects within the electronic device, (e.g., busses and possibly bridges). Thus, the non-transitory machine-readable storage media (e.g., memory 1304) of a given electronic device typically stores code (e.g., instructions 1314) for execution on the set of one or more processors 1302 of that electronic device. One or more parts of various embodiments may be implemented using different combinations of software, firmware, and/or hardware.

A computing device 1300 can include some type of display element 1306, such as a touch screen or liquid crystal display (LCD), although many devices such as portable media players might convey information via other means, such as through audio speakers, and other types of devices such as server end stations may not have a display element 1306 at all. As discussed, some computing devices used in some embodiments include at least one input and/or output component(s) 1312 able to receive input from a user. This input component can include, for example, a push button, touch pad, touch screen, wheel, joystick, keyboard, mouse, keypad, or any other such device or element whereby a user is able to input a command to the device. In some embodiments, however, such a device might be controlled through a combination of visual and/or audio commands and use a microphone, camera, sensor, etc., such that a user can control the device without having to be in physical contact with the device.

Figure 14:
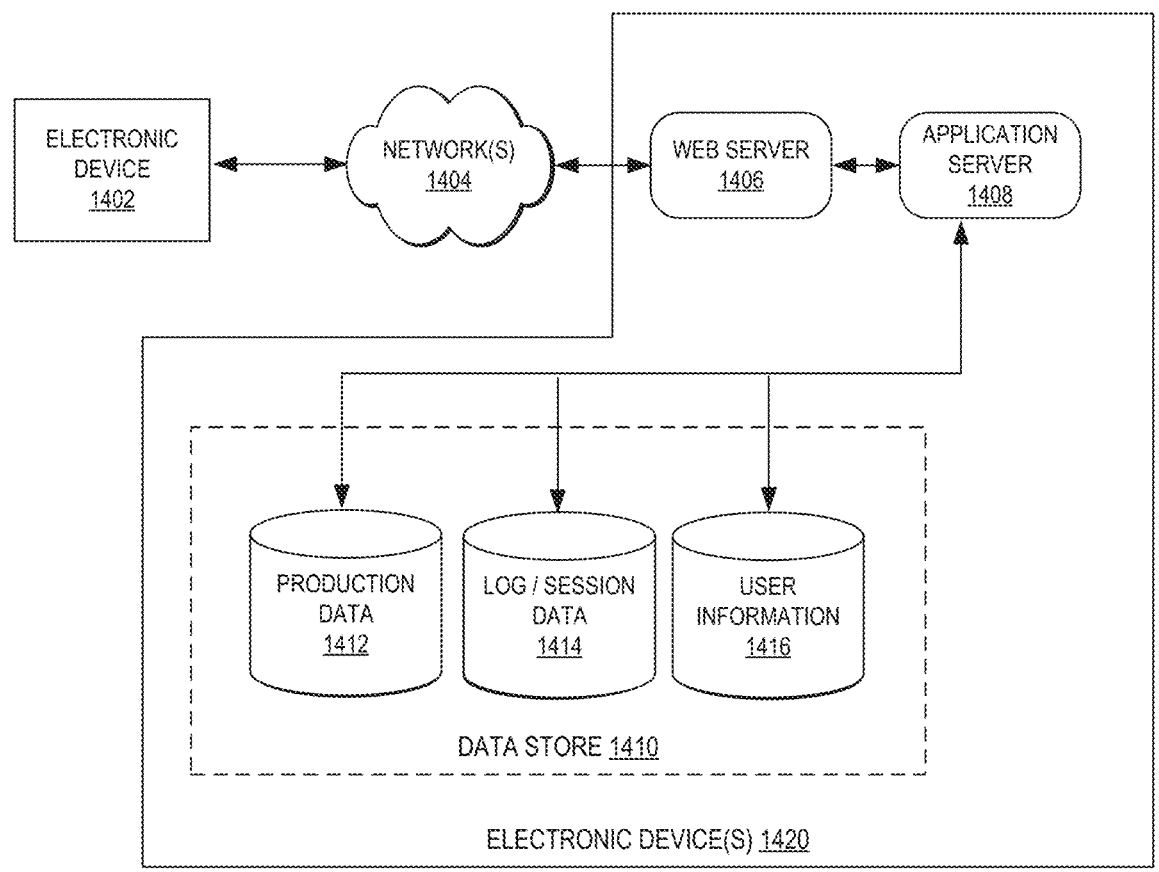
FIG. 14 illustrates an example of an environment for implementing aspects in accordance with various embodiments.

As discussed, different approaches can be implemented in various environments in accordance with the described embodiments. For example, FIG. 14 illustrates an example of an environment 1400 for implementing aspects in accordance with various embodiments. For example, in some embodiments requests to telemedicine service 117 are HyperText Transfer Protocol (HTTP) requests that are received by a web server (e.g., web server 1406), and the users, via electronic devices, may interact with the provider network via a web portal provided via the web server 1406 and application server 1408. As will be appreciated, although a web-based environment is used for purposes of explanation, different environments may be used, as appropriate, to implement various embodiments. The system includes an electronic client device 1402, which may also be referred to as a client device and can be any appropriate device operable to send and receive requests, messages or information over an appropriate network 1404 and convey information back to a user of the device 1402. Examples of such client devices include personal computers (PCs), cell phones, handheld messaging devices, laptop computers, set-top boxes, personal data assistants, electronic book readers, wearable electronic devices (e.g., glasses, wristbands, monitors), and the like. The one or more networks 1404 can include any appropriate network, including an intranet, the Internet, a cellular network, a local area network, or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network 1404 includes the Internet, as the environment includes a web server 1406 for receiving requests and serving content in response thereto, although for other networks an alternative device serving a similar purpose could be used, as would be apparent to one of ordinary skill in the art.

The illustrative environment includes at least one application server 1408 and a data store 1410. It should be understood that there can be several application servers, layers, or other elements, processes or components, which may be chained or otherwise configured, which can interact to perform tasks such as obtaining data from an appropriate data store. As used herein the term "data store" refers to any device or combination of devices capable of storing, accessing and retrieving data, which may include any combination and number of data servers, databases, data storage devices and data storage media, in any standard, distributed or clustered environment. The application server 1408 can include any appropriate hardware and software for integrating with the data store 1410 as needed to execute aspects of one or more applications for the client device 1402 and handling a majority of the data access and business logic for an application. The application server 1408 provides access control services in cooperation with the data store 1410 and is able to generate content such as text, graphics, audio, video, etc., to be transferred to the client device 1402, which may be served to the user by the web server in the form of HyperText Markup Language (HTML), Extensible Markup Language (XML), JavaScript Object Notation (JSON), or another appropriate unstructured or structured language in this example. The handling of all requests and responses, as well as the delivery of content between the client device 1402 and the application server 1408, can be handled by the web server 1406. It should be understood that the web server 1406 and application server 1408 are not required and are merely example components, as structured code discussed herein can be executed on any appropriate device or host machine as discussed elsewhere herein.

The data store 1410 can include several separate data tables, databases, or other data storage mechanisms and media for storing data relating to a particular aspect. For example, the data store illustrated includes mechanisms for storing production data 1412 and user information 1416, which can be used to serve content for the production side. The data store 1410 also is shown to include a mechanism for storing log or session data 1414. It should be understood that there can be many other aspects that may need to be stored in the data store, such as page image information and access rights information, which can be stored in any of the above listed mechanisms as appropriate or in additional mechanisms in the data store 1410. The data store 1410 is operable, through logic associated therewith, to receive instructions from the application server 1408 and obtain, update, or otherwise process data in response thereto. In one example, a user might submit a search request for a certain type of item. In this case, the data store 1410 might access the user information 1416 to verify the identity of the user and can access a production data 1412 to obtain information about items of that type. The information can then be returned to the user, such as in a listing of results on a web page that the user is able to view via a browser on the user device 1402. Information for a particular item of interest can be viewed in a dedicated page or window of the browser.

The web server 1406, application server 1408, and/or data store 1410 may be implemented by one or more electronic devices 1420, which can also be referred to as electronic server devices or server end stations and may or may not be located in different geographic locations. Each of the one or more electronic devices 1420 may include an operating system that provides executable program instructions for the general administration and operation of that device and typically will include computer-readable medium storing instructions that, when executed by a processor of the device, allow the device to perform its intended functions. Suitable implementations for the operating system and general functionality of the devices are known or commercially available and are readily implemented by persons having ordinary skill in the art, particularly in light of the disclosure herein.

The environment in one embodiment is a distributed computing environment using several computer systems and components that are interconnected via communication links, using one or more computer networks or direct connections. However, it will be appreciated by those of ordinary skill in the art that such a system could operate equally well in a system having fewer or a greater number of components than are illustrated in FIG. 14. Thus, the depiction of the environment 1400 in FIG. 14 should be taken as being illustrative in nature and not limiting to the scope of the disclosure.

In the preceding description, various embodiments are described. For purposes of explanation, specific configurations and details are set forth in order to provide a thorough understanding of the embodiments. However, it will also be apparent to one skilled in the art that the embodiments can be practiced without the specific details. Furthermore, well-known features can be omitted or simplified in order not to obscure the embodiment being described.

Bracketed text and blocks with dashed borders (e.g., large dashes, small dashes, dot-dash, and dots) are used herein to illustrate optional operations that add additional features to some embodiments. However, such notation should not be taken to mean that these are the only options or optional operations, and/or that blocks with solid borders are not optional in certain embodiments.

Reference numerals with suffix letters (e.g., 1118A-1118N) can be used to indicate that there can be one or multiple instances of the referenced entity in various embodiments, and when there are multiple instances, each does not need to be identical but may instead share some general traits or act in common ways. Further, the particular suffixes used are not meant to imply that a particular amount of the entity exists unless specifically indicated to the contrary. Thus, two entities using the same or different suffix letters might or might not have the same number of instances in various embodiments.

References to "one embodiment," "an embodiment," "an example embodiment," etc., indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Moreover, in the various embodiments described above, unless specifically noted otherwise, disjunctive language such as the phrase "at least one of A, B, or C" is intended to be understood to mean either A, B, or C, or any combination thereof (e.g., A, B, and/or C). Similarly, language such as "at least one or more of A, B, and C" (or "one or more of A, B, and C") is intended to be understood to mean A, B, or C, or any combination thereof (e.g., A, B, and/or C). As such, disjunctive language is not intended to, nor should it be understood to, imply that a given embodiment requires at least one of A, at least one of B, and at least one of C to each be present.

Unless otherwise explicitly stated, articles such as "a" or "an" should generally be interpreted to include one or multiple described items. Accordingly, phrases such as "a device configured to" or "a computing device" are intended to include one or multiple recited devices. Such one or more recited devices can be collectively configured to carry out the stated operations. For example, "a processor configured to carry out operations A, B, and C" can include a first processor configured to carry out operation A working in conjunction with a second processor configured to carry out operations B and C.

The specification and drawings are, accordingly, to be regarded in an illustrative rather than a restrictive sense. It will, however, be evident that various modifications and changes can be made thereunto without departing from the broader spirit and scope of the disclosure as set forth in the claims.

What is claimed is:

1. A computer-implemented method comprising:
   obtaining a first image of an ailment using a camera coupled to a mobile device;
   determining an alignment class of the first image of the ailment using an alignment classifier executing on the mobile device;
   generating alignment instructions based on the alignment class and a reference image associated with the ailment using at least one machine learning model executing on the mobile device;
   providing the alignment instructions via the mobile device, wherein the alignment instructions indicate a change in at least one of position or attitude of the mobile device relative to the ailment;
   obtaining a second image of the ailment using the camera after the mobile device has been repositioned relative to the ailment based on the alignment instructions;
   determining the second image of the ailment is aligned with the reference image; and
   sending the second image to an agent device via a telemedicine service of a provider network.

2. The computer-implemented method of claim 1, further comprising:
   sending a request to the telemedicine service to initiate a session with a provider, wherein the telemedicine service identifies an available provider associated with the agent device and enables a secure connection to be established between the mobile device and the agent device.

3. A computer-implemented method comprising:
   determining an alignment class of a first image of an object using an alignment classifier executing on a user device;
   providing alignment instructions based on the alignment class and a reference image associated with the object using at least one machine learning model executing on the user device, wherein the alignment instructions indicate a change in at least one of position or attitude of the mobile device relative to the object;

obtaining an aligned image of the object after the user device has been repositioned relative to the object based on the alignment instructions; and sending the aligned image to an agent device via a telemedicine service of a provider network.

4. The computer-implemented method of claim 3, wherein the alignment instructions are displayed via the user device or reproduced audibly via the user device.

5. The computer-implemented method of claim 3, further comprising:

capturing video data using a camera coupled to a user device, wherein the first image of the object is a first frame of the video data and wherein the aligned image of the object is a second frame of the video data.

6. The computer-implemented method of claim 3, wherein determining an alignment class of a first image of an object using an alignment classifier executing on a user device, further comprises:

determining the reference image most likely to match the object depicted in the first image; and determining an alignment type associated with the reference image.

7. The computer-implemented method of claim 6, further comprising:

determining the alignment type is normal alignment;

determining a first surface normal associated with the object;

determining a second surface normal associated with the user device;

determining a center of mass difference vector between the object and the user device; and generating the alignment instructions to align the user device and the object based at least on the first surface normal, the second surface normal, and the center of mass difference vector.

8. The computer-implemented method of claim 7, wherein generating the alignment instructions to align the user device and the object based at least on the first surface normal, the second surface normal, and the center of mass difference vector, further comprises:

generating a first alignment instruction to change a position of the user device such that a dot product of the first surface normal and the center of mass difference vector is approximately equal to 1; and generating a second alignment instruction to change the attitude of the user device such that a dot product of the first surface normal and the second surface normal is approximately equal to −1.

9. The computer-implemented method of claim 7, wherein determining a first surface normal associated with the object, further comprises:

determining a location associated with the object using a localization model, wherein the object is a medical ailment visible on a body part of a patient, and wherein the localization model is a neural network trained to identify ailments in image data;

determining an alignment model of the body part of the patient using an alignment model, wherein the alignment model is a neural network trained to generate a geometric representation of a body part in image data; and determining the first surface at the location associated with the object based on the geometric representation of the body part.

10. The computer-implemented method of claim 6, further comprising:

determining the alignment type is reference point alignment;

estimating a first plurality of reference points associated with the first image using an image annotation model;

identifying a second plurality of reference points associated with the reference image;

determining a translation between the first plurality of reference points and the second plurality of reference points based on point set alignment; and generating the alignment instructions based at least on the translation.

11. The computer-implemented method of claim 3, wherein sending the aligned image to an agent device via a telemedicine service of a provider network, further comprises:

sending ranks associated with a plurality of reference images to the agent device, wherein each rank indicates a likelihood of a match between the aligned image and a corresponding reference image, wherein the agent device displays the aligned image and at least one of the reference images to a provider for review.

12. A system comprising:

a first one or more electronic devices to implement a telemedicine service in a multi-tenant provider network; and a user device including a camera, the user device communicatively coupled to the telemedicine service in the multi-tenant provider network, the user device including instructions that upon execution cause the user device to:

determine an alignment class of a first image of an object using an alignment classifier executing on a user device;

provide alignment instructions based on the alignment class and a reference image associated with the object using at least one machine learning model executing on the user device, wherein the alignment instructions indicate a change in at least one of position or attitude of the mobile device relative to the object;

obtain an aligned image of the object after the user device has been repositioned relative to the object based on the alignment instructions; and send the aligned image to an agent device via a telemedicine service of a provider network.

13. The system of claim 12, wherein the alignment instructions are displayed via the user device or reproduced audibly via the user device.

14. The system of claim 12, wherein the instructions, when executed, further cause the user device to:

capture video data using the camera, wherein the first image of the object is a first frame of the video data and wherein the aligned image of the object is a second frame of the video data.

15. The system of claim 12, wherein to determine an alignment class of a first image of an object using an alignment classifier executing on a user device, the instructions, when executed, further cause the user device to:

determine the reference image most likely to match the object depicted in the first image; and determine an alignment type associated with the reference image.

16. The system of claim 15, wherein the instructions, when executed, further cause the user device to:

determine the alignment type is normal alignment;

determine a first surface normal associated with the object;

determine a second surface normal associated with the user device;
determine a center of mass difference vector between the object and the user device; and
generate the alignment instructions to align the user device and the object based at least on the first surface normal, the second surface normal, and the center of mass difference vector.

17. The system of claim 16, wherein to generate the alignment instructions to align the user device and the object based at least on the first surface normal, the second surface normal, and the center of mass difference vector, the instructions, when executed, further cause the user device to:
generate a first alignment instruction to change a position of the user device such that a dot product of the first surface normal and the center of mass difference vector is approximately equal to 1; and
generate a second alignment instruction to change the attitude of the user device such that a dot product of the first surface normal and the second surface normal is approximately equal to −1.

18. The system of claim 16, wherein to determine a first surface normal associated with the object, the instructions, when executed, further cause the user device to:
determine a location associated with the object using a localization model, wherein the object is a medical ailment visible on a body part of a patient, and wherein the localization model is a neural network trained to identify ailments in image data;
determine an alignment model of the body part of the patient using an alignment model, wherein the alignment model is a neural network trained to generate a geometric representation of a body part in image data; and
determine the first surface at the location associated with the object based on the geometric representation of the body part.

19. The computer-implemented method of claim 15, wherein the instructions, when executed, further cause the user device to:
determine the alignment type is reference point alignment;
estimate a first plurality of reference points associated with the first image using an image annotation model;
identify a second plurality of reference points associated with the reference image;
determine a translation between the first plurality of reference points and the second plurality of reference points based on point set alignment; and
generate the alignment instructions based at least on the translation.

20. The system of claim 12, wherein to send the aligned image to an agent device via a telemedicine service of a provider network, the instructions, when executed, further cause the user device to:
send ranks associated with a plurality of reference images to the agent device, wherein each rank indicates a likelihood of a match between the aligned image and a corresponding reference image, wherein the agent device displays the aligned image and at least one of the reference images to a provider for review.

* * * * *